United States Patent [19]

Dickinson et al.

[11] 4,350,703
[45] Sep. 21, 1982

[54] β-LACTAM ANTIBACTERIAL AGENTS

[75] Inventors: Kay H. Dickinson, Reading; Terence C. Smale, Epsom Downs; Robert Southgate, Warnham, all of England

[73] Assignee: Beecham Group Limited, England

[21] Appl. No.: 222,282

[22] Filed: Jan. 5, 1981

Related U.S. Application Data

[62] Division of Ser. No. 82,427, Oct. 5, 1979, abandoned, which is a division of Ser. No. 887,844, Mar. 17, 1978, abandoned.

[30] Foreign Application Priority Data

Mar. 19, 1977 [GB] United Kingdom ............... 11747/77

[51] Int. Cl.³ .................... C07D 487/04; A61K 37/40
[52] U.S. Cl. ............................. 424/274; 260/239 A; 260/245.2 T; 424/114; 542/429; 542/443
[58] Field of Search .................. 260/245.2 T; 424/274

[56] References Cited

U.S. PATENT DOCUMENTS

| | | | |
|---|---|---|---|
| 4,206,219 | 6/1980 | Christensen et al. | 260/245.2 T |
| 4,223,038 | 9/1980 | Smale | 260/245.2 T |
| 4,260,627 | 4/1981 | Christensen et al. | 260/245.2 T |
| 4,262,009 | 4/1981 | Christensen et al. | 260/245.2 T |
| 4,289,696 | 9/1981 | Smale | 260/245.2 T |

OTHER PUBLICATIONS

Bateson et al.; J. Chem. Soc., Chem. Commun., pp. 185–186 (1980).

*Primary Examiner*—Mary C. Lee
*Attorney, Agent, or Firm*—Jacobs & Jacobs

[57] ABSTRACT

Compounds are described of the formula (II):

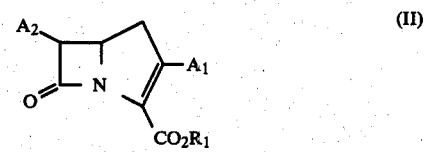

wherein $R_1$ is a group such that $CO_2R_1$ is an ester group; $A_1$ is a hydrogen atom; and $A_2$ is a group $CR_2R_3R_4$ wherein $R_2$ is a hydrogen atom or a hydroxyl group; $R_3$ is a hydrogen atom or a lower alkyl group; and $R_4$ is a hydrogen atom or a lower alkyl group, a benzyl group, a phenyl group or is joined to $R_3$ to form part of a $C_{5-7}$ carboxylic ring or is a group of the formula $CH(OH)R_5$ or $CHX$ wherein $R_5$ is a hydrogen atom or lower alkyl group and $X$ is an oxygen atom or a $CR_6R_7$ group where $R_6$ is a hydrogen atom or a lower alkyl, phenyl, CN, $CO_2R_8$ where $R_8$ is a lower alkyl, phenyl or benzyl group and $R_7$ is a hydrogen atom or a lower alkyl group or is joined to $R_6$ to form part of a $C_{5-7}$ carbocyclic ring. These compounds have been found to possess antibacterial properties. The preparation of these compounds is described.

20 Claims, No Drawings

β-LACTAM ANTIBACTERIAL AGENTS

CROSS-REFERENCE

This is a division of Ser. No. 082,427 filed Oct. 5, 1979 which is a divisional of Ser. No. 887,844 filed Mar. 17, 1978, now both abandoned.

The present invention relates to β-lactam antibacterials, to compositions containing them, to the process for their preparation and to compounds useful as intermediates in that process.

British Pat. No. 1,467,413 discloses that the compound of the formula (I):

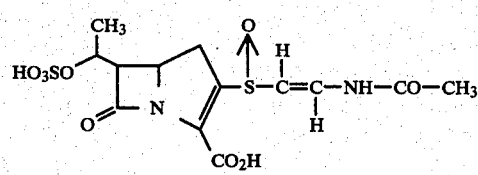

and its salts may be obtained via the fermentation of strains of *Streptomyces olivaceus*. We have now found that a distinct class of synthetic antibacterial agents may be prepared.

Accordingly the present invention provides the compounds of the formula (II):

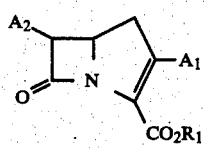

wherein $R_1$ is a group such that $CO_2R_1$ is an ester group; $A_1$ is a hydrogen atom or a methyl group; and $A_2$ is a hydrogen atom or a group of $CR_2R_3R_4$ wherein $R_2$ is a hydrogen atom or a hydroxyl group; $R_3$ is a hydrogen atom or a lower alkyl group; and $R_4$ is a hydrogen atom or a lower alkyl group, a benzyl group, a phenyl group or is joined to $R_3$ to form part of a $C_{5-7}$ carbocyclic ring or is a group of the formula $CH(OH)R_5$ or CHX wherein $R_5$ is a hydrogen atom or lower alkyl group and X is an oxygen atom or a $CR_6R_7$ group where $R_6$ is a hydrogen atom or a lower alkyl, phenyl, CN, $CO_2R_8$ or $CO.R_8$ where $R_8$ is a lower alkyl, phenyl or benzyl group and $R_7$ is a hydrogen atom or a lower alkyl group or is joined to $R_6$ to form part of a $C_{5-7}$ carbocyclic ring.

When used herein the term "lower" means the group contains up to 8 carbon atoms. When used herein the term "lower alkyl" more suitably means a group of up to 6 carbon atoms which is most suitably a straight chain group of up to 4 carbon atoms.

One suitable sub-group of compounds of the formula (II) is that of the formula (III):

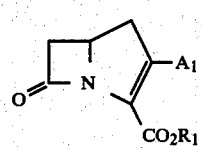

wherein $R_1$ and $A_1$ are as defined in relation to formula (II):

Suitably $A_1$ is a methyl group. Suitably $A_1$ is a hydrogen atom.

A further suitable sub-group of compounds of the formula (II) is that of the formula (IV):

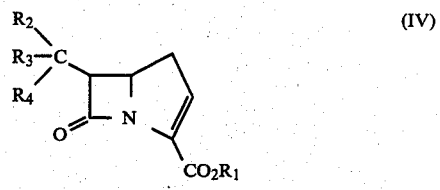

wherein $R_1$, $R_2$, $R_3$ and $R_4$ are as defined in relation to formula (II).

Suitably $R_2$ is a hydrogen atom. Suitably $R_2$ is a hydroxyl group. Suitable values for $R_4$ include the hydrogen atom and the methyl, ethyl, n-propyl, phenyl, CHO, CH=CHCO$_2$R$_9$, CH=CHCOR$_9$, and CH=CHR$_{10}$ groups wherein $R_9$ is a methyl, ethyl or benzyl group and $R_{10}$ is a hydrogen atom or a methyl, ethyl or benzyl group.

Suitable values for $R_3$ include the hydrogen atom and the methyl, ethyl and n-propyl groups.

Favourably $R_3$ is a hydrogen atom or a methyl group.

Favourably $R_4$ is a hydrogen atom or a methyl group.

A suitable sub-group of compounds of the formulae (IV) is that of the formula (V):

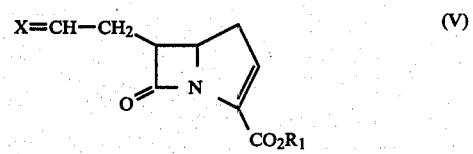

wherein $R_1$ and X are as defined in relation to formula (II).

Suitably X is an oxygen atom. Suitably X is a $CR_6R_7$ group where $R_6$ and $R_7$ are defined as in relation to formula (II).

Favourably $CR_6R_7$ is a CHCOR$_9$ or CHCO$_2$R$_9$ group where $R_9$ is as defined in relation to formula (IV). Favourably $CR_6R_7$ is a CHCN group.

A further apt sub-group of compounds of the formula (IV) is that of the formula (VI):

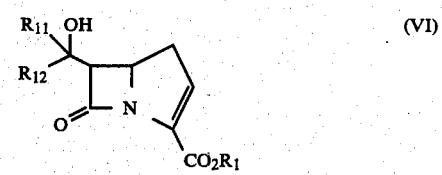

wherein $R_1$ is as defined in relation to formula (IV), $R_{11}$ is a hydrogen atom or a lower alkyl group and $R_{12}$ is a hydrogen atom or a lower alkyl group.

Suitably $R_{11}$ is a hydrogen atom or a methyl group. Suitably $R_{12}$ is a hydrogen atom or a methyl group.

Yet another apt sub-group of compounds of the formula (III) is that of the formula (VII):

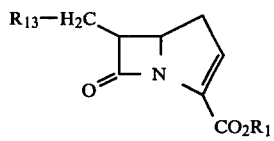

wherein R₁ is as defined in relation to formula (II) and R₁₃ is a hydrogen atom or a methyl, ethyl or hydroxymethyl group.

The compounds of the formula (IV)-(VII) may have the cis-configuration about the β-lactam ring. The compounds of the formulae (IV)-(VII) may alternatively have the transconfiguration about the β-lactam ring. If desired these compounds may be presented as mixtures of cis- and trans-compounds although it is not normally preferred to so do.

The compounds of the formula (II)-(VII) are generally provided as mixtures of 5R and 5S forms but separated forms are also within the ambit of this invention.

Suitable values for R₁ in the compounds of the formula (II)-(VII) include alkyl groups of up to 12 carbon atoms, alkenyl groups of up to 8 carbon atoms, alkynyl groups of up to 8 carbon atoms or a phenyl or benzyl group or one of the aforementioned groups substituted by a lower alkoxyl, lower acyloxyl, halogen or nitro group.

Aptly R₁ is a lower alkyl group optionally substituted by a lower alkoxyl group.

Aptly R₁ is a benzyl group optionally substituted by a lower alkoxyl or nitro group or chlorine atom.

Favoured values for R₁ include the groups of the sub-formulae (a) or (b):

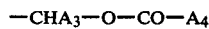

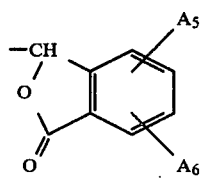

wherein A₃ is a hydrogen atom or a methyl group; A₄ is a lower alkyl, lower alkoxyl, phenyl, phenoxyl, benzyl or benzyloxyl group; A₅ is a hydrogen atom or a methyl or methoxyl group and A₆ is a hydrogen atom and methyl or methoxyl group.

Certain preferred groups R₁ include the methyl, methoxymethyl, benzyl, p-methoxybenzyl, acetoxymethyl, pivaloyloxymethyl, α-ethoxycarbonyloxyethyl, phthalidyl, phenacyl and phthalimidomethyl groups.

A favoured group R₁ is the phthalidyl group.

A further favoured group R₁ is the benzyl group.

Another favoured group R₁ is the p-nitrobenzyl group.

This invention also provides an antibacterial pharmaceutical composition which comprises a compound of the formula (II) and a pharmaceutically acceptable carrier.

Most suitably the composition will be in unit dosage form and will comprise 25-1000 mg and more usually 50-500 mg of a compound of the formula (II).

Preferably the compound of the formula (II) present in such compositions will be in-vivo hydrolysable to the parent acid or its salt.

The compositions of this invention may beneficially also comprise a penicillin or cephalosporin. Certain particularly suitable penicillins for use in these compositions include amoxycillin trihydrate and sodium amoxycillin.

The compositions of this invention may be used for the treatment of bacterial infections due to susceptible bacteria such as gram positive bacteria such as *Staphylococcus aureus*.

The compositions may be administered in conventional manner, for example parenterally or by intramammary administration for the treatment of mastitis in cattle.

The present invention also provides a process for the preparation of a compound of the formula (II) which process comprises the ring closing elimination of the elements of O=PA₇A₈A₉ from a compound of the formula (VIII):

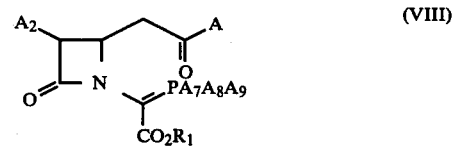

wherein R₁, A₁ and A₂ l are as defined in relation to formula (II) and A₇, A₈ and A₉ are lower alkyl, phenyl or methoxyphenyl groups.

Aptly A₇, A₈ and A₉ are all phenyl groups. Other apt values for each of A₇, A₈ and A₉ is the p-methoxyphenyl group.

Suitably A₂ is a hydrogen atom.

Suitably A₂ is a group CR₂R₃R₄ as defined in relation to formula (IV).

The elimination reaction tends to occur spontaneously at relatively low temperatures, for example −20° C. to 0° C. when A₁ is a hydrogen atom or at a higher temperature, for example at about 100° C. when A₁ is methyl.

The solvent used for the proceeding process will be an inert organic solvent such as ethyl acetate, benzene or toluene.

The compounds of the formula (VIII) wherein A₁ is hydrogen may be prepared by a reaction sequence such as:

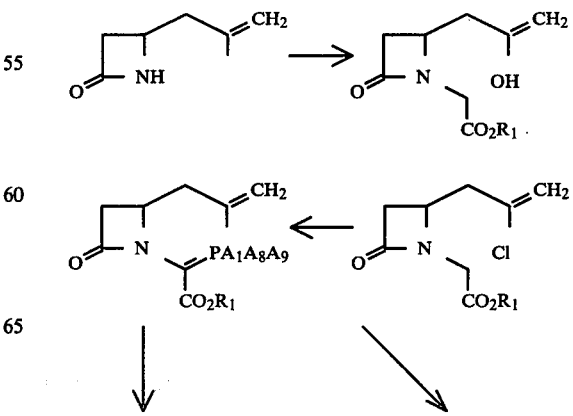

-continued

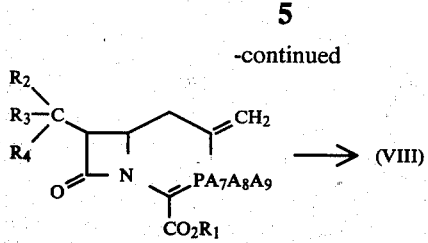

This invention provides a process for the preparation of a compound of the formula (VIII) as hereinbefore defined which process comprises the ozonolysis in the presence of excess trifluoroacetic acid of a compound of the formula (IX):

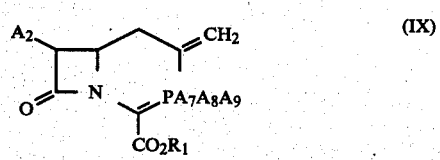

wherein $R_1$, $A_1$, $A_2$, $A_7$, $A_8$ and $A_9$ are as defined in relation to formula (VIII) and thereafter neutralising the trifluoroacetic acid.

This ozonolysis is normally carried out in an inert solvent such as ethyl acetate, or methylene chloride.

The process is normally carried out at a depressed temperature, for example $-80°$ to $-20°$ C., more usually at about $-70°$ to $-50°$ C. In general ozone is passed through the solution until a light blue colour is produced. At this point excess ozone may be removed by passing through an inert gas. The intermediate ozonide may now be reduced by the addition of a conventional reducing agent such as triphenylphosphine. The trifluoroacetic acid should now be neutralised for example by the addition of a solution of a base such as sodium bicarbonate solution at about 0° C.

Once the neutralisation is complete the reaction is usually allowed to warm to ambient temperature under which conditions the compound spontaneously cyclises.

This invention also provides a process for the preparation of a compound of the formula (IX) as hereinbefore defined where $A_2$ is a $CR_2R_3R_4$ group which process comprises reacting a compound of the formula (X):

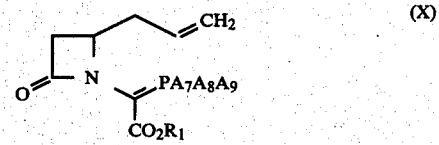

wherein $A_7$, $A_8$, $A_9$ and $R_1$ are as defined in relation to formula (VIII) with a base to generate an anion of the formula (XI):

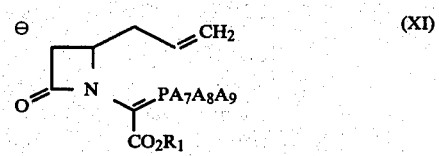

wherein $A_7$, $A_8$, $A_9$ and $R_1$ are as defined in relation to formula (VIII); which is then reacted with a compound of the formula (XII), (XIII) or (XIV):

wherein $R_3$, $R_4$ and $R_5$ are as defined in relation to formula (II) and Y is a moiety readily displaced by a nucleophile.

Suitable values for Y include Cl, Br, I. $OSO_2CH_3$ $O.SO_2.C_6H_4CH_3$ or the like. Particularly suitable values for Y include Cl, Br and I.

The generation and reaction of the anion of the formula (XI) is brought about in an inert organic medium under aprotic conditions. Suitable solvents for the reaction include hydrocarbons such as hexane, tetrahydrofuran, dimethoxyethane, formdimethylamide, hexamethylphosphorus triamide or mixtures thereof.

Since the anion is a highly reactive species its generation and reaction are normally affected at a depressed temperature, for example at or below 0° C., more suitably $-80°$ to $-60°$ C.

The base used to generate the anion of the formula (XI) will be a strong base of low nucleophilicity. Suitable bases include lithium alkyls such as lithium butyl, lithium amides such as lithium di-isopropylamine or lithium hexamethyldisilylamide or the like.

Once formed the anion may be quenched by the addition of the dry compound of the formula (XII), (XIII) or (XIV). The compound of the formula (XII), (XIII) or (XIV) may be added neat or dissolved in a dry inert solvent.

It is most suitable to carry out the preceding reactions under an inert atmosphere, for example under dry nitrogen or dry argon.

The preceding normally produces a mixture of the cis- and trans-compounds of the formula (XV) and (XVI):

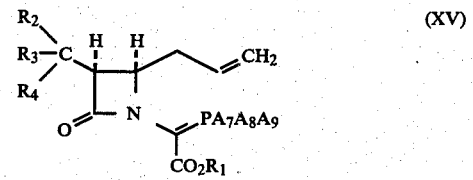

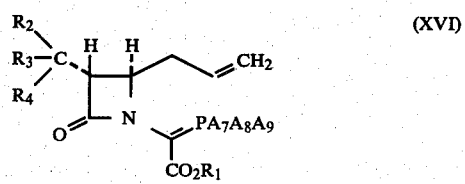

in admixture with their $C_5$ enantiomers.

These cis- and trans-substituted compounds can generally be separated from each other by chromatography, for example over silica gel gradiently eluting with solvent mixtures such as ethyl acetate/hexane.

The compounds of the formula (X) as hereinbefore defined may be prepared by the reaction of a compound of the formula (XVII):

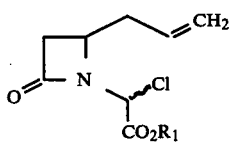
(XVII)

wherein $R_1$ is as defined in relation to formula (II) with a phosphine of the formula $PA_7A_8A_9$ wherein $A_7$, $A_8$ and $A_9$ are as defined in relation to formula (X).

This reaction is normally carried out in an inert solvent such as dioxane, tetrahydrofuran or the like in the presence of at least 1 equivalent of a base such as 2,6-lutidine or like base of relatively low nucleophilicity. In general the reaction is carried out at a non-extreme temperature such as about 5°–35° C.

The compound of formula (XVII) may be prepared by the reaction of thionyl chloride on a corresponding compound of the formula (XVIII):

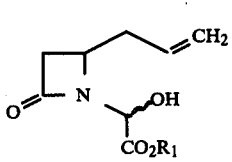
(XVIII)

wherein $R_1$ is as defined in relation to formula (II).

This reaction takes place under similar conditions to the preparation of the compound of the formula (X) except that a depressed temperature, for example −30° to −10° C., is used.

The compound of the formula (XVIII) may be prepared by the reaction of a compound of the formula (XIX):

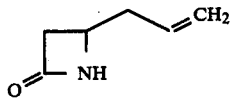
(XIX)

and a compound of the formula (XX):

(XX)

wherein $R_1$ is defined as in relation to formula (II).

This preceding reaction is conveniently carried out by reacting the compounds together in refluxing benzene in such a manner that any water present is continuously removed.

The compounds of the formula (II) wherein $CR_2R_3R_4$ is a $CH_2.CH=X$ group wherein X is as defined in relation to formula (II) may also be prepared by the following reaction sequence:

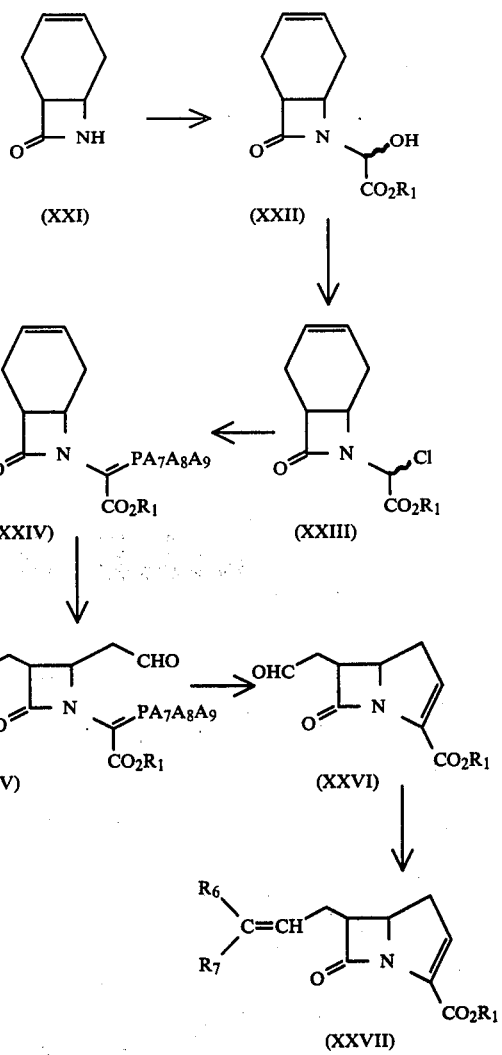

The compounds of the formula (XXI) may be obtained by the method of Paquett et al, J. Amer. Chem. Soc., 90, 2897, (1968).

The compounds of the formula (XXI) prepared in this manner have the cis-configuration at the ring junction and this configuration is preserved in the compounds of the formulae (XXII)-(XXVII).

The compounds of the formula (XXII) may be prepared by the reaction of a compound of the formula (XXI) with a compound of the formula (XX) as hereinbefore defined under conditions similar to those described for the reaction of a compound of the formula (XIX) and (XX).

Reaction of a compound of the formula (XXII) with thionyl chloride under conditions similar to those described for the reaction of thionyl chloride with a compound of the formula (XVIII) may be used to prepare the compounds of the formula (XXIII).

The compounds of the formula (XXIII) may be converted into the compounds of the formula (XXIV) by reaction with a phosphine of the formula $PA_7A_8A_9$ under conditions similar to those used for the preparation of a compound of the formula (X).

The present invention also provides a process for the preparation of the compounds of the formula (XXV):

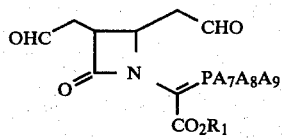 (XXV)

wherein $A_7$, $A_8$, $A_9$ and $R_1$ are as defined in relation to formula (X) which process comprises the ozonolysis of a compound of the formula (XXIV):

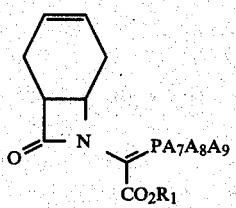 (XXIV)

wherein $R_1$, $A_7$, $A_8$ and $A_9$ are as defined in relation to formula (IX).

The ozonolysis reaction may be brought about under conditions similar to those described for the ozonolysis of the compounds of the formula (IX).

Once formed the compounds of the formula (XXV) undergo spontaneous cyclisation with elimination of the elements of a compound of the formula $O=PA_7A_8A_9$ and the formation of a compound of the formula (XXVI). This cyclisation reaction also forms part of this invention.

The compounds of the formula (XXVI) tend to be somewhat unstable so that it is often more suitable to react them in situ with an agent such as a compound of the formula (XXVIII):

$$R_6 \atop R_7 ^{\displaystyle \diagdown} C = PPh_3 \quad (XXVIII)$$

or chemically equivalent agents wherein $R_6$ and $R_7$ are as defined in relation to formula (II).

This reaction of the compounds of the formula (XXVI) and (XXVIII) occurs under conventional reaction conditions for reaction of an aldehyde and a phosphorane and gives the olefins of formula (XXVII).

The compounds of the formula (XVIII) and (XXII) may also be prepared by the reaction of a compound of the formula (XIX) or (XXI) with glyoxylic acid and thereafter esterifying the resulting compound of the formula (XXIXa) or (XXIXb)

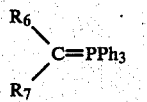 (XXIXa)

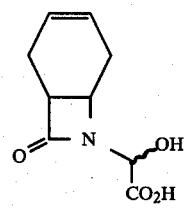 (XXIXb)

in a conventional manner.

Certain trans substituted compounds may be prepared by the following reaction scheme in which an allyl halide such as allyl bromide is reacted with the anion (XI) in similar manner to the alkylations previously described. The ozonolysis of the resulting compound may be carried out as described for ozonolysis of a compound of the formula (XXIV) and the ring closure of the compound of the formula (XXXI) may be carried out as described for the compound of the formula (XXV).

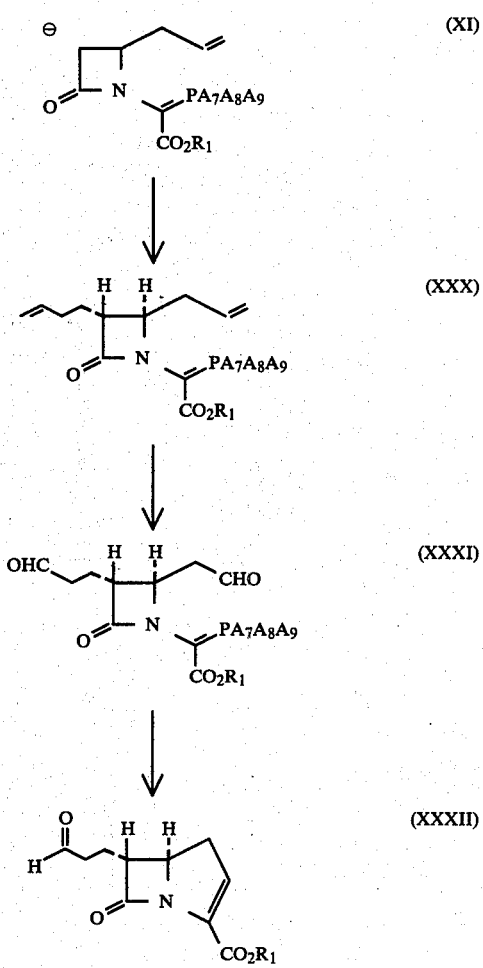

The compounds of the formula (VIII) wherein $A_1$ is a methyl group may be prepared by a reaction sequence such as

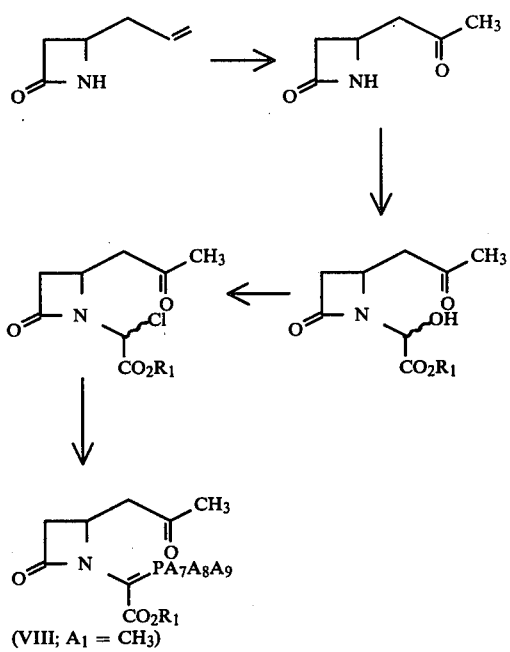

H-(Propan-2-one)azetidin-2-one may be prepared as described in Example 22 herein. Reaction of this compound with a glyoxylic acid ester to yield a compound of the formula (XXXIII) may be carried out under conditions similar to those described for an analogous reaction of a corresponding vinyl compound. (Alternatively the 4-(Propan-2-one)azetidin-2-one may be reacted with glyoxylic acid and the resulting compound esterified thereafter). The reaction of the resulting hydroxy compound with thionyl chloride and the reaction of the resulting chloro compound with a phosphene may be brought about in a manner similar to that described hereinbefore for the preparation of a compound of the formula (X).

The following Examples illustrate the invention:

EXAMPLE 1

Benzyl 6-(2-oxoethyl)-7-oxo-1-azabicyclo[3.2.0]hept-2-ene-2-carboxylate

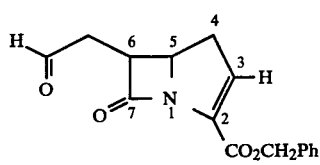

(i) 7-(1-Hydroxy-1-benzyloxycarbonylmethyl)-8-oxo-7-azabicyclo[4,2,0]oct-3-ene

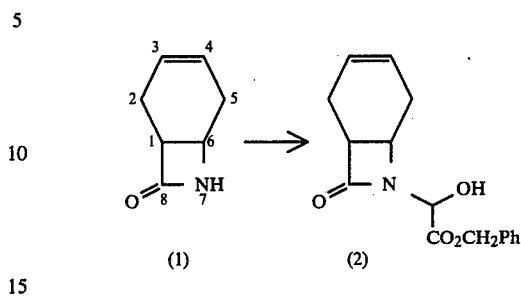

Benzyl glyoxylate (2.73 g) was refluxed in benzene (25 ml) with provision for the removal of water. After 45 minutes 8-oxo-7-azabicyclo[4,2,0]oct-3-ene (1) (ref: I. A. Paquette and T. Kakihana, *J. Amer. Chem. Soc.*, 1968, 90, 2897) (1.23 g) was added and refluxing continued for 3 hours. Removal of solvent under reduced pressure followed by chromatography gave two separate isomers of the alcohol (2)(90%) Isomer I, m.p. 92°–93°, $\nu_{max}$ (CHCl$_3$)3450, 1750 (b) cm$^{-1}$. δppm (CDCl$_3$) 1.76–2.73 (4H, m, 2-CH$_2$), 3.12–3.33 (1H, m, β-lactam proton), 3.76–3.93 (1H, m, β-lactam proton), 4.40 (1H, d, J 6 Hz, exch., D$_2$O), 5.16 (2H, s CH$_2$), 5.47 (1H, d, J 6 Hz collapsing to s on D$_2$O exch., C$\underline{H}$-OH), 5.67–5.83 (2H, m, CH=CH), 7.34 (5H, Ar). M$^+$ at m/e 287 (Found: C, 66.2; H, 5.9; N, 4.9. C$_{16}$H$_{17}$NO$_4$ requires C, 66.9; H, 6.0; N, 4.9%). Isomer II, m.p. 100°–101°, $\nu_{max}$ (CHCl$_3$) 3450, 1750 (b), δppm (CDCl$_3$) 1.80–2.63 (4H, m,2-CH$_2$), 3.13–3.36 (1H, m, β-lactam proton), 3.93–4.13 (1H, m, β-lactam proton), 4.20 (1H, bs, exch., D$_2$O), 5.16 (2H, s, CH$_2$), 5.50 (1H, b, sharpening to s on D$_2$O exchange), 5.50–6.00 (2H, m, CH=CH), 7.34 (5H, Ar). H$^+$ at m/e (Found: C, 67.2; H, 6.0; N, 4.8. C$_{16}$H$_{17}$NO$_4$ requires C, 66.9; H, 6.0; N, 4.9%).

(ii) 7-(1-Benzyloxycarbonyl-1-triphenylphosphoranylidenemethyl)-8-oxo-7-azabicyclo[4,2,0]oct-3-ene

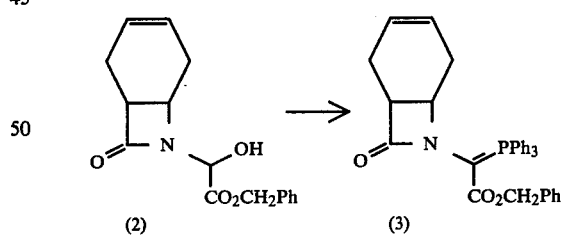

The alcohol (2, as mixture of isomers, 2.2 g), in THF (50 ml) was cooled to −20°. Lutidine (1.5 g) was added followed by thionyl chloride (1.0 ml). After stirring at −20° for 20 min, the solution was filtered and evaporated to dryness; final removal of the last traces of excess thionyl chloride was by evaporation twice from toluene. The residue in dioxan (20 ml) was treated with triphenylphosphine (4.02 g) and lutidine (1.64 g) and left stirring overnight at room temperature. The lutidine hydrochloride was separated by filtration, and the filtrate evaporated to dryness and chromatographed to give (3,1.5 g) as an amorphous solid, $\nu_{max}$(CHCl$_3$) 1730, 1620 cm$^{-1}$.

(iii) Benzyl 6-(2-oxoethyl)-7-oxo-1-azabicyclo[3,2,0]hept-2-ene-2-carboxylate

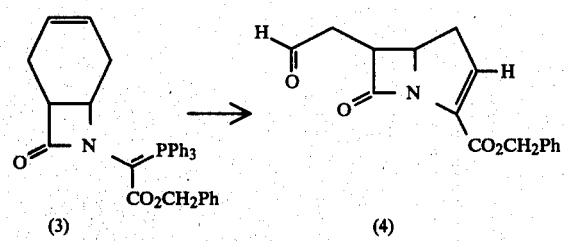

The phosphorane (3, 0.2 g) in ethyl acetate (10 ml) was treated with trifluoroacetic acid (0.25 ml). The solution was cooled (−65°) and treated with ozone until the reaction solution showed a slight blue colouration. Argon was blown through the solution to remove excess ozone, and then triphenylphosphine (0.1 g) was added. After five minutes the reaction was transferred to an ice-bath and stirred vigorously with aqueous (5%) sodium bicarbonate solution (10 ml) for 45 minutes. The organic phase was separated, dried, evaporated and chromatographed to give the product (4, 42 mg as a gum), $\nu_{max}$ (CHCl$_3$) 1780, 1725, 1610 cm$^{-1}$. δppm (CDCl$_3$) 2.50–3.00 (4H, m, 2×CH$_2$), 3.87–4.11 (1H, m, C6-H), 4.46 (1H, dt, J 6 Hz, 9 Hz C5-H; collapses to d, J 6 Hz on irradiation at δ2.60); 5.21 (2H, s, benzyl CH$_2$), 6.45 (1H, t, J 2 Hz, C3-H), 7.30 (5H, s, Ar), 9.70 (1H, s, CHO). M+ at m/e 285. The β-lactamase inhibition I$_{50}$ values in μg/ml for (4) were as follows:

Enterobacter P99: 1.6
Pseudomonas aeruginosa A: >>40
Proteus mirabilis C889: 2.1
Klebsiella aerogenes E70: >>40
Escherichia coli JT4: <1.2
Pseudomonas dalgleish: 1.0
Staphylococcus aureus Russell: >10

EXAMPLE 2

Benzyl 6-(3-methoxycarbonyl-2-propen-1-yl)-7-oxo-1-azabicyclo[3,2,0]hept-2-ene-2-carboxylate

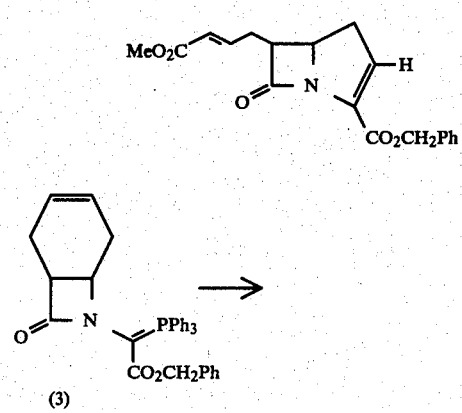

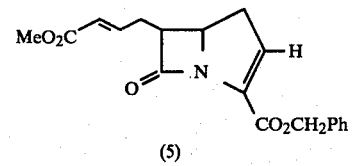

The phosphorane (3,0.2 g) in ethyl acetate (10 ml) was treated with trifluoroacetic acid (0.25 ml) and subjected to ozonolysis and work up as in Example 1 (iii) the crude product containing (4) was dissolved in chloroform (5 ml) and treated with methoxycarbonylmethylene triphenylphosphorane (0.124 g) and left for 1 hour at room temperature. The solution was evaporated to dryness and chromatographed to give the product (5) (45 mg), m.p. 81°–82° (from ether), $\nu_{max}$ (CHCl$_3$)1780, 1720, 1650, 1610 cm$^{-1}$. δppm (CDCl$_3$) 2.68 (2H, dd, J 9 Hz, 3 Hz, C4-CH$_2$; collapsing to d J 3 Hz on irradiation at δ4.3); 2.40–2.90 (2H, m, C6 side-chain CH$_2$), 3.67 (3H, s, OMe), 3.67–3.74 (1H, m, C6-H), 4.35 (1H, dt, J 6 Hz, 9 Hz, C5-H, collapsing to d J 6 Hz on irradiation at δ2.6); 5.20 (2H, s, benzyl CH$_2$), 5.80 (1H, d, J 15 Hz, trans MeO$_2$CCH=CH—), 6.45 (1H, t, J 3 Hz, C3-H, collapsing to s on irradiation at δ2.6), 6.84 (1H, dt, J 15 Hz, 6 Hz, trans —CH=CH—CH$_2$), 7.32 (5H, s, Ar). (Found: M, 341.1270. C$_{19}$H$_{19}$NO$_5$ requires M, 341.1263).

The minimum concentrations of this compound required to inhibit the growth of the following bacteria are given below:

| Organism | MIC (μg/ml) agar |
| --- | --- |
| Bacillus subtilis A | 20 |
| Citrobacter freundii E8 | 20 |
| Klebsiella aerogenes A | 20 |
| Shigella sonnei MB 11967 | 20 |
| Staph. aureus Russell | 2 |
| Staph. aureus 1517 | 2 |

A small amount (6 mg) of the cis-isomer (about the C-6 side-chain double bond) of (5) was also obtained.

EXAMPLE 3

2,2,2-Trichloroethyl-6-(3-methoxycarbonyl-2-propen-1-yl)-7-oxo-1-azabicyclo[3,2,0]hept-2-ene-2-carboxylate

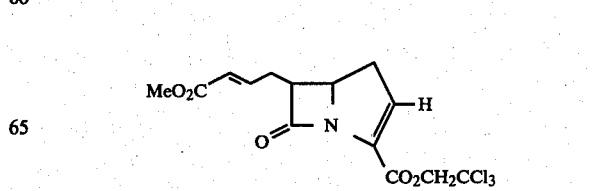

(i)

7-(1-Hydroxy-1-2,2,2-trichloroethoxycarbonylmethyl)-8-oxo-7azabicyclo [4,2,0]oct-3-ene

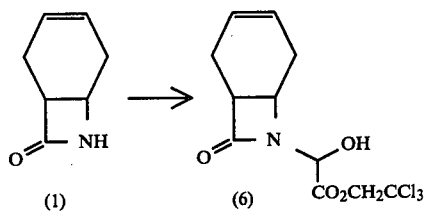

2,2,2-Trichloroethylglyoxylate (0.78 g) was refluxed in benzene (15 ml) with provision for the removal of water (0.5 hrs). The azetidinone (1) (0.287 g) was added and refluxing continued for 1 hour. Removal of the solvent and chromatography gave the alcohol (6) (80%). Isomer I m.p. 85°–88°, $\nu_{max}$ (CHCl$_3$) 3500, 1770 (ester), 1750 ($\beta$-lactam)cm$^{-1}$. $\delta$ppm (CDCl$_3$)2.00–2.80 (4H, m, 2×CH$_2$), 3.30–3.40 (1H, m, $\beta$-lactam proton), ca 3.70 (1H, bs, exch, D$_2$O, OH), 4.10–4.25 (1H, m, $\beta$-lactam proton), 4.80 (2H, s, CH$_2$), 5.50 (1H, s, C<u>H</u>), 5.72–5.91 (2H, m, CH=CH). (Found: C, 40.3; H, 3.7; N, 4.2. C$_{11}$H$_{12}$Cl$_3$NO$_4$ requires C, 40.2; H, 3.7; N, 4.3%). Isomer II m.p. 119°–121°, had similar spectroscopic properties.

(ii)

7-(1-Trichloroethoxycarbonyl-1-triphenylphosphoranylidenemethyl)-8-oxo-7-azabicyclo[4,2,0]oct-3-ene

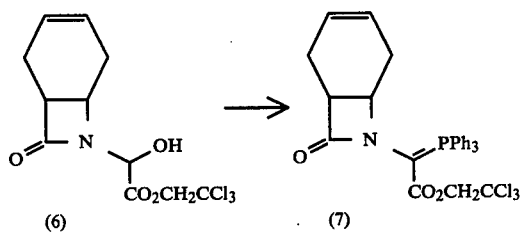

The alcohol (6) (6.0 g as a mixture of isomers) in THF (75 ml) was converted to the chloride as in example 1 (ii) using thionyl chloride (2.61 ml) and lutidine (4.25 ml). The crude chloride in dioxan (75 ml) was reacted with triphenylphosphine (9.6 g) and lutidine (4.25 ml) as for the benzyl ester to give the phosphorane (7), (6.0 g) as a foam, $\nu_{max}$ (CHCl$_3$) 1740, 1630Cm$^{-1}$.

(iii)

2,2,2-Trichloroethyl-6-(3-methoxycarbonyl-2-propen-1-yl)-7-oxo-1-azabicyclo[3,2,0]hept-2-ene-2-carboxylate

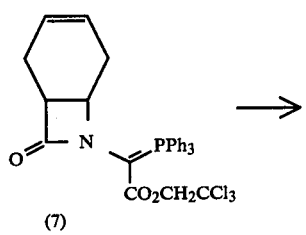

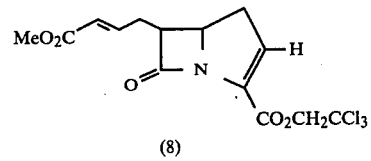

The phosphorane (7) (0.2 g) was dissolved in EtAc (10 ml) and trifluoroacetic acid (1 ml) and subjected to ozonolysis and work up as for the benzyl ester in example1 (iii). The crude reaction product in chloroform (3 ml) was treated with carbomethoxymethylene triphenylphosphorane (117 mg) and left at R.T. for 0.5 hours. Evaporation and chromatography gave (8) (40 mg) m.p. 101°–102°, $\mu$max (CHCl$_3$) 1785, 1735, 1720, 1660, 1615 cm$^{-1}$. $\delta$ ppm (CDCl$_3$) 2.74 (2H, dd, J 10 Hz, 3 Hz, C4-CH$_2$), 2.30–2.90 (2H, m, CH$_2$), 3.65 (3H, s, OMe), 3.60–3.90 (1H, m, C6-H), 3.38 (1H, dt, J 6 Hz, 10 Hz, C5-H), 4.70 and 4.86 (2H, Abq, J 12 Hz, C<u>H$_2$</u>CCl$_3$), 5.80 (1H, d, J 15 Hz plus further slight coupling trans MeO$_2$C-C<u>H</u>=CH-CH$_2$), 6.60 (1H, t, J 3 Hz, C3-H), 6.84 (1H, dt, J 15 Ez, 6 Hz, trans CH=C<u>H</u>-CH$_2$). $\lambda_{max}$ (EtOH) 209 nm ($\epsilon$ 12,100), 273 nm ($\epsilon$ 3110).

The concentrations of this compound required to inhibit the growth of the following bacteria are given below.

| Organism | $\mu$g/ml (agar) |
| --- | --- |
| B. Subtilis A | 20 |
| Citrobacter freundii E8 | 20 |
| Klebsiella aerogenes A | 20 |
| Shigella sonnei MB 11967 | 20 |
| Staph. aureus Oxford | $\leq$2 |
| Staph. aureus Russell | $\leq$2 |
| Staph. aureus 1517 | $\leq$2 |
| Strep faecalis I | 20 |
| Strep pneumoniae | 20 |
| Strep pyogenes CN10 | 20 |

A small amount (6 mg, m.p. 70°–72°) of the cis-isomer (about the C-6 double bond) was also obtained.

EXAMPLE 4

Benzyl 6-(2-hydroxy-2-propyl)-7-oxo-1-azabicyclo[3,2,0[hept-2-ene-2-carboxylate

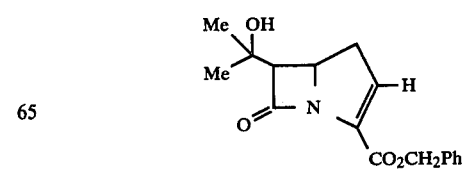

(i) 4-Allyl-1-(1-benzyloxycarbonyl-1-triphenylphosphoranylidenemethyl)-3-(2-hydroxy-2-propyl)azetidin-2-one

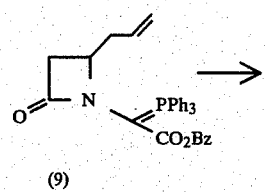

(9)

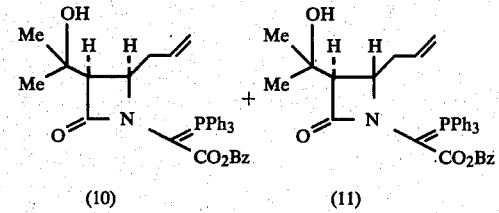

(10)   (11)

A solution of N-isopropylcyclohexylamine (0.60 g) in dry tetrahydrofuran (10 ml) was stirred under argon and cooled to −78° C. This was treated with a 2.5 M solution of n-butyl lithium in n-hexane (1.70 ml). After ten minutes, a solution of 4-allyl-1-(1-benzyloxycarbonyl-1-triphenylphosphoranylidenemethyl)azetidin-2-one (9) (1.00 g) in dry tetrahydrofuran (10 ml) was added. Five minutes was allowed for the formation of the C(3) carbanion which was then quenched by the addition of dry acetone (0.71 ml). The cooling bath was then removed and the mixture stirred for a further ten minutes before it was neutralised with acetic acid (0.56 g). The solvent was evaporated under reduced pressure and the residue chromatographed on silica gel 60 (<230 mesh), eluting with ethyl acetate/60°-20° petroleum ether mixtures grading from 1:1 to 7:3. This gave a mixture of the cis and trans-isomers of 4-allyl-1-(1-benzyloxycarbonyl-1-triphenylphosphoranylidenemethyl)-3-(2-hydroxy-2-propyl)azetidin-2-one (0.76 g; 71%) (10) and (11), $\nu_{max}$ (CHCl$_3$) 3000, 1735 and 1620 cm$^{-1}$.

It was possible to obtain a substantial separation of the cis- and trans-isomers by further chromatography on silica gel 60 (<230 mesh), eluting with ethyl acetate/60°-80° petroleum ether mixtures grading from 1:1 to 7:3.

(ii) Benzyl 6-(2-hydroxy-2-propyl)-7-oxo-1-azabicyclo]3,2,0]hept-2-ene-2-carboxylate

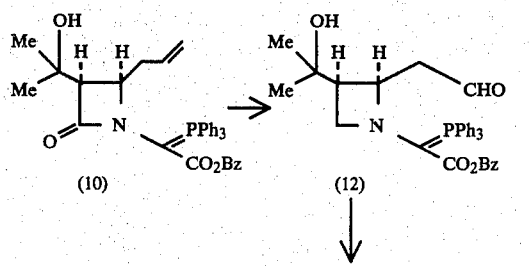

(10)   (12)

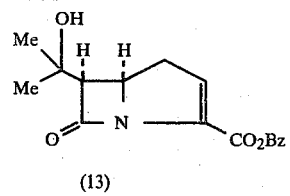

(13)

The cis-isomer of 4-allyl-1-(1-benzyloxycarbonyl-1-triphenylphosphoranylidenemethyl)-3-(2-hydroxy-2-propyl)azetidin-2-one (10) (0.188 g) was dissolved in ethyl acetate (14 ml). An excess of trifluoroacetic acid (0.37 g) was added and the mixture cooled to −78° C. Ozone was passed into the reaction mixture until it was pale blue in colour. Argon was then bubbled through the solution until all the excess ozone had been removed. A solution of triphenylphosphine (0.085 g) in ethyl acetate was added and argon bubbled through the mixture for a further ten minutes. The reaction flask was then transferred to an ice bath and a saturated aqueous solution of sodium bicarbonate (20 ml) was added and the mixture stirred vigourously under argon for thirty minutes. The ethyl acetate layer was separated, washed with brine and dried.

The solution containing (12) was left at room temperature for thirty-six hours. During this time, the cyclisation reaction was followed by thin-layer chromatography and it was seen that a slow moving spot gradually decreased in intensity along with an increase in the intensity of a faster moving spot which corresponded to the required cis-product. The ethyl acetate was evaporated off under reduced pressure and the residue was purified by chromatography on silica gel 60 (<230 mesh), eluting with ethyl acetate/60°-80° petroleum ether 1:1. The product was a crystalline material (0.048 g; 49%), which could be recrystallised from ethyl acetate/60°-80° petroleum ether; m.p. 122°-124°. $\nu_{max}$ (CHCl$_3$) 2950, 1770 and 1720 cm$^{-1}$; $\lambda_{max}$ (EtOH) 273 nm (ε 4800). δ ppm (CDCl$_3$) 7.36 (5H, br. s, phenyl) 6.59 (1H, t, J 2½ Hz, C3-H), 5.28 and 5.30 (2H, inside signals of ABq, —CH$_2$—Ph), 4.35 (1H, dt, J 6½ and 9 Hz, C5-H), 3.83 (1H, ddd, J 18, 9 and 2½ Hz, C4-H), 3.59 (1H, d J6½ Hz, C6-H), 2.68 (1H, ddd, J 18, 9 and 2½ Hz, C4-H), 1.74 (1H, br. s, —OH), 1.30 and 1.54 (6H, two singlets, C-CH$_3$'s). $\lambda_{max}$ (ethanol). (M$^+$ at m/e 301.1315 C$_{17}$H$_{19}$NO$_4$ requires 301.1314. Found: C, 67.7; H, 6.5; N, 4.5%. C$_{17}$H$_{19}$NO$_4$ requires C, 67.8; H, 6.4; N, 4.7%).

The concentrations of this compound required to inhibit the growth of the following bacteria are given below.

| Organism | μg/ml (agar) |
| --- | --- |
| *Enterobacter cloaceae* N1 | 20 |
| *Klebsiella aerogenes* A | ≦2 |
| *Serratia marcescens* US20 | 20 |
| *Shigella sonnei* MB 11967 | ≦2 |
| *Staph. aureus* Oxford | ≦2 |
| *Staph. aureus* Russell | ≦2 |

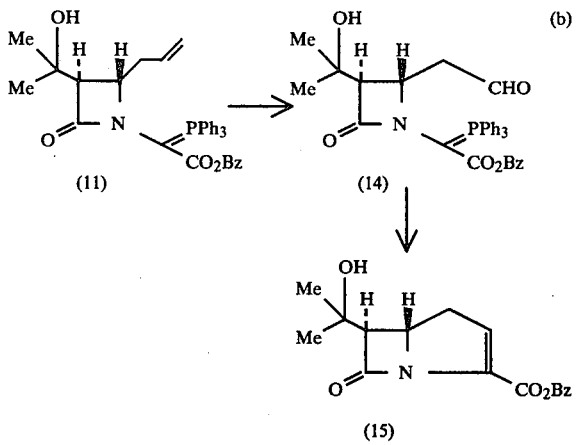

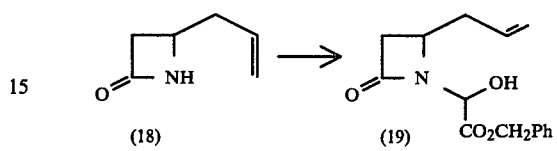

(iv) Preparation of 4-allyl-1-(1-hydroxy-1-benzyloxycarbonylmethyl)azetidin-2-one The trans-isomer of 4-alkyl-1-(1-benzyloxycarbonyl-1-triphenylphosphoranylidenemethyl)-3-(2-hydroxy-2-propyl)azetidin-2-one (11) (0.365) was treated as in (a) above. In this case, however, the formation of the bicyclic system was complete after stirring the basified reaction mixture from the ozonolysis for thirty minutes. The required product (0.048 g; 25%) was obtained after chromatography; $\nu_{max}$ (CHCl$_3$) 2950, 1780 and 1720 cm$^{-1}$; Y ppm (CDCl$_3$) 7.28 (5H, br, phenyl), 6.36 (1H, t, J 2 Hz, C3-H), 5.20 (2H, s, —CH$_2$Ph), 4.20 (1H, dt J 3 and 8 Hz, C5-H), 3.16 (1H, d J 3 Hz, C6-trans H), 2.95 and 2.65 (2H, two ddd's J 18, 8 and 2 Hz, C4-H's), 1.78 (1H, br. s, —OH), 1.30 and 1.37 (6H, two singlets, C-CH$_3$'s); (M$^+$ at m/e 301.1303. C$_{17}$H$_{19}$NO$_4$ requires 301.1314).

(c) The procedure described in section ii (a) was carried out on the mixture of the cis- and trans-isomers of 4-allyl-1-(1-benzyloxycarbonyl-1-triphenylphosphoranylidenemethyl)-3-(2-hydroxy-2-propyl)azetidin-2-one (0.76 g) as obtained in Example(a). After work-up and chromatographic separation, pure cis (0.045 g; 11%) and trans (0.100 g; 25%) isomers of benzyl 6-(2-hydroxy-2-propyl)-7-oxo-1-azabicyclo[3,2,0]hept-2-ene-2-carboxylate were obtained.

(iii) Preparation of 4-allyl azetidin-2-one

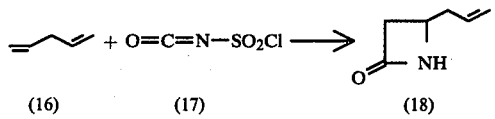

1,4 Pentadiene (16) (30 g) and chlorosulphonyl isocyanate (17) (35.4 ml) were mixed and allowed to stand at room temperature for 3 days, in a pressure bottle. The thick, dark syrup, obtained was diluted with methylene chloride (500 ml) and added dropwise to a stirred solution of sodium sulphite (66 g) in water (240 ml). The pH was maintained between 6.5 and 7.5 by the addition of 10% aqueous potassium hydroxide (600 ml in total). The lower organic phase was separated and the aqueous phase extracted (×2) with ethyl acetate. The combined organic extracts were dried over magnesium sulphate, filtered, and evaporated to give the crude azetidinone (18) as a red oil (16.05 g). This was sufficiently pure for use in subsequent reactions e.g. Example 4(iv), but could be further purified by distillation b.p. 76°-80°/0.2 mm. $\nu_{max}$ (CHCl$_3$) 3490, 1770 (strong), 1630 (weak) cm$^{-1}$. δ ppm (CDCl$_3$) 2.39 (2H, t, J 6 Hz, CH$_2$), 2.61 (1H, ddd, J 14 Hz, 2 Hz, 1.5 Hz, collapsing with D$_2$O to dd, J 14 Hz, 2 Hz, C3-H), 3.10 (1H, ddd, J 14 Hz, 5 Hz, 2 Hz, collapsing with D$_2$O to dd, J 14 Hz, 5 Hz, C3-H), 3.55-3.91 (1H, m, C4-H), 4.98-6.21 (3H, complex pattern, CH=CH$_2$), 6.67 (1H, broad s, exch. D$_2$O) (Found: M, 111.0683. C$_6$H$_9$NO requires M, 111.0684).

(iv) Preparation of 4-allyl-1-(1-hydroxy-1-benzyloxycarbonylmethyl)azetidin-2-one Benzyl glyoxylate hydrate (6 g) in benzene (120 ml) was refluxed for 0.5 hours in a Dean-Stark apparatus to remove the water. The azetidinone (18) (2.13 g) was added and the reaction mixture refluxed for 4 hours. The solution was cooled, evaporated, and chromatographed on silica gel, eluting with ethyl acetate-petroleum ether mixtures to give a colourless oil (5.6 g) consisting mainly of the isomers of (19) and sufficiently pure for use in subsequent reactions. Rechromatography of a small portion of this oil, eluting with chloroform gave (19) as an oil. $\nu_{max}$ (CHCl$_3$) 3420, 1750 (strong), 1640 (weak) cm$^{-1}$. δ ppm (CDCl$_3$) 1.90-3.05 [4H, m, including δ 2.53 (1H, dd, J 15 Hz, 2 Hz, C3-H), 2.92 (1H, dd, J 15 Hz, 5 Hz, C3-H), obscuring 2H, CH$_2$], 4.52 (1H, broad, s, exch. D$_2$O,-OH), 4.85-5.90 [6H, m, including δ 5.40, (1H, broad, collapsing with D$_2$O to singlet, H-C-OH)+complex pattern for CH$_2$Ph and CH=CH$_2$], 7.29 (5H, s).

(v) Preparation of 4-allyl-1-(1-benzyloxycarbonyl-1-triphenylphosphoranylidenemethyl)azetidin-2-one

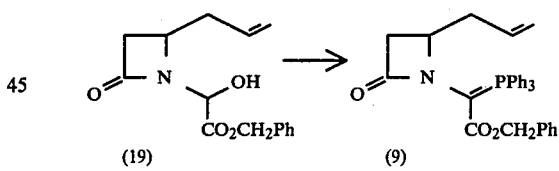

A stirred solution of the alcohol (19) (6.6 g) in dry tetrahydrofuran (200 ml), under argon, was cooled to −20°, and treated with lutidine (5.13 g) in tetrahydrofuran (10 ml). Thionyl chloride (5.70 g) in tetrahydrofuran (20 ml) was added dropwise. After allowing to reach 0° over 20 minutes, the precipitated solid was filtered off, washing with dry toluene.

The combined filtrate and washings were evaporated to dryness and the residue taken up in dry toluene, filtered and evaporated. The gum obtained was taken up in dioxan (200 ml) and treated with triphenylphosphine (12.6 g) and lutidine (5.53 ml). After stirring under argon at room temperature for 3 hours and standing overnight, the precipitated solid was filtered off. The filtrate was evaporated to dryness. Chromatography on silica gel eluting with ethyl acetate-petroleum ether mixtures, gave the required phosphorane, initially as a foam, which crystallised from ether (5.70 g) m.p. 150°-6°. $\nu_{max}$ (CHCl$_3$) 1730, 1638, 1610 cm$^{-1}$.

EXAMPLE 5

Benzyl 6-(1-hydroxyethyl)-7-oxo-1-azabicyclo[3,2,0]hept-2-ene-2-carboxylate

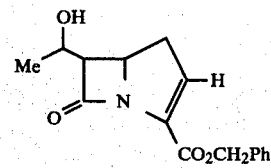

(i) 4-Allyl-1-(1-benzyloxycarbonyl-1-triphenylphosphoranylidenemethyl)-3-(1-hydroxyethyl)azetidin-2-one

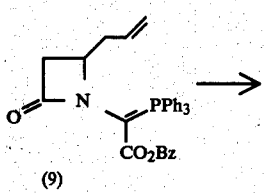

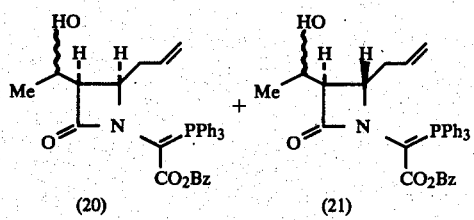

A solution of N-isopropylcyclohexylamine (0.60 g) in dry tetrahydrofuran (10 ml) was stirred under argon and cooled to −78° C. This was treated with a 2.5 M solution of n-butyl lithium in n-hexane (1.70 ml). After ten minutes, a solution of 4-allyl-1-(1-benzyloxycarbonyl-1-triphenylphosphoranylidenemethyl)azetidin-2-one (9) (1.00 g) in dry tetrahydrofuran (10 ml) was added. Five minutes was allowed for the formation of the C(3) carbanion which was then quenched by the addition of acetaldehyde (0.54 ml). The mixture was stirred under argon for a further ten minutes before it was neutralized with acetic acid (0.56 g). The solvent was evaporated under reduced pressure and the residue chromatographed on silica gel 60 (<230 mesh) eluting with ethyl acetate/cyclohexane mixtures grading from 1:1 to pure ethyl acetate. This gave a mixture of the cis and trans-isomers of 4-allyl-1-(1-benzyloxycarbonyl-1-triphenylphosphoranylidenemethyl)-3-(1-hydroxyethyl)azetidin-2-one (0.71 g; 65%) (20) and (21); $\nu_{max}$ (CHCl$_3$) 3000, 1735 and 1620 cm$^{-1}$.

(ii) Benzyl 6-(1-hydroxyethyl)-7-oxo-1-azabicyclo[3,2,0]hept-2-ene-2-carboxylate

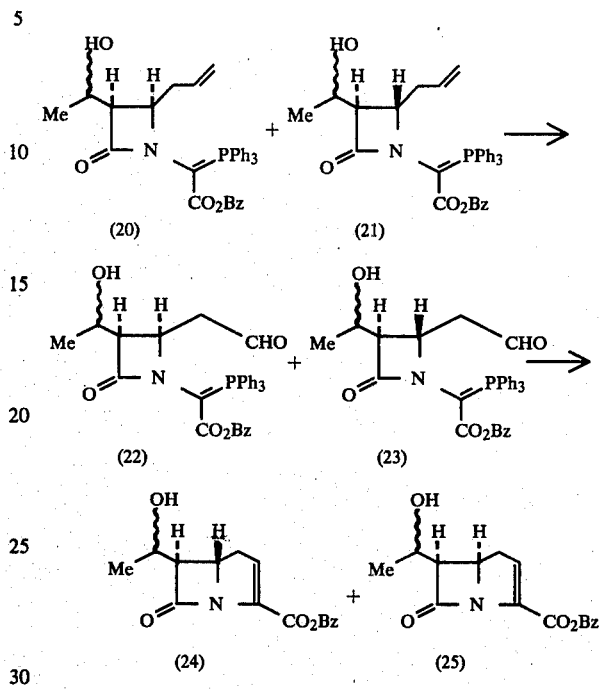

A mixture of cis and trans-isomers of 4-allyl-1-(1-benzyloxycarbonyl-1-triphenylphosphoranylidenemethyl)-3-(1-hydroxyethyl)azetidin-2-one (0.79 g) as obtained in section (i) was dissolved in redistilled ethyl acetate (70 ml). An excess of trifluoroacetic acid (1.60 g) was added and the mixture cooled to −78° C. Ozone was passed into the reaction mixture until it was pale blue in colour. Argon was then bubbled through the solution until all the excess ozone had been removed. A solution of triphenylphosphine (0.37 g) in ethyl acetate was added and argon bubbled through the mixture for a further ten minutes. The reaction flask was then transferred to an ice bath and a saturated aqueous solution of sodium bicarbonate (104 ml) was added to generate the phosphoranes (22) and (23). The mixture was stirred vigourously under argon for thirty minutes. The ethyl acetate layer was separated, washed with brine and dried over sodium sulphate.

The solution was left to stand at room temperature for three days to allow the cyclisation reactions to proceed to completion. The ethyl acetate was then evaporated off under vacuum and the residue chromatographed on silica gel 60 (<230 mesh) (80 g), eluting with ethyl acetate/60°-80° petroleum ether mixtures grading from 3:7 to 7:3. Only two of the four possible diastereoisimers of benzyl 6-(1-hydroxyethyl)-7-oxo-1-azabicyclo[3,2,0]hept-2-ene-2-carboxylate could be isolated from the reaction mixture; these were one cis and one trans-isomer about the β-lactam ring. The pure cis-isomer (25) (0.030 g; 7.4%) was a crystalline material which could be recrystallized from ethyl acetate/6-0°-80° petroleum ether; m.p. 94°-99° C. $\nu_{max}$ (CHCl$_3$) 3000, 1775, 1725 and 1615 cm$^{-1}$; δ ppm ((CD$_3$)$_2$CO) 7.22-7.40 (5H, m, phenyl), 6.46 (1H, t J 2½ Hz, C3-H), 5.17 (2H, s, —CH$_2$—Ph), 4.25 (1H, ddd J 10, 8 and 6 Hz, —C5—H) overlapping with 3.94-4.23 (1H, m, sidechain —CH), 3.51 (1H, dd J 6 and 6 Hz, C6-H), 3.25 (1H, ddd J 18, 8 and 2½ Hz, C4-H), 2.63 (1H, ddd J 18, 10 and 2½ Hz, C4-H), 1.25 (3H, d J 6 Hz, —CH₃) (M⁺ at m/e 287.1150. C₁₆H₁₇NO₄ requires 287.1157).

The pure trans-isomer (24) (0.07 g; 17.4%) had ν$_{max}$ (CHCl₃) 3000, 1780, 1725 and 1610 cm⁻¹; δ ppm ((CD₃)₂CO) 7.2-7.5 (5H, m, phenyl), 6.36 (1H, t, J 2½ Hz, C3-H), 5.17 (2H. s, —CH₂—Ph), 4.20 (1H, td J 9 and 3 Hz, C5-H) overlapping with 3.94-4.23 (1H, m side chain —CH), 3.31 (1H, dd J 3½ and 3 Hz, C6-H), 2.96 (1H, s, —OH), 2.77 (2H, dd J 9 and 2½ Hz, C4-Ps), 1.25 (3H, d J 6 Hz, —CH₃) (M⁺ at m/e 287.1156. C₁₆H₁₇NO₄ requires 287.1157).

EXAMPLE 6

Benzyl 6-(1-hydroxy-1-phenylmethyl)-7-oxo-1-azabicyclo[3,2,0]hept-2-ene-2-carboxylate

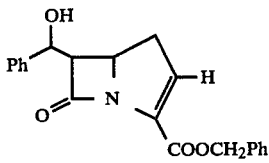

(i) 4-Allyl-1-(1-benzyloxycarbonyl-1-triphenylphosphoranylidenemethyl)-3-(1-hydroxy-1-phenylmethyl)azetidin-2-one

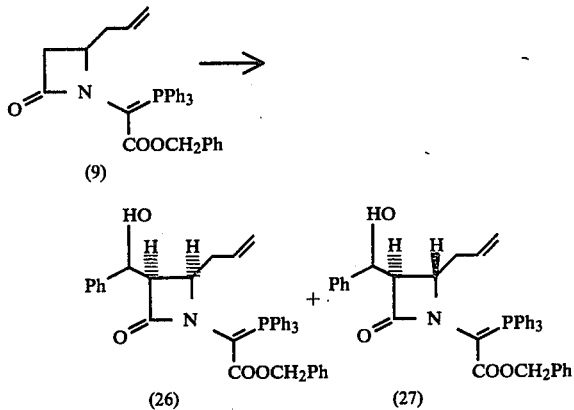

A solution of N-isopropylcyclohexylamine (1.20 g) in dry tetrahydrofuran (20 ml) was stirred under argon and cooled to −78°. This was treated with a 1.6 M solution of n-butyl-lithium in n-hexane (5.30 ml). After ten minutes, a solution of 4-allyl-1-(1-benzyloxycarbonyl-1-triphenylphosphoranylidenemethyl)azetidin-2-one (9) (2.00 g) in dry tetrahydrofuran (40 ml) was added. Five minutes were allowed for the formation of the C(3) carbanion which was then quenched by the addition of benzaldehyde (1.0 ml). The solution was kept at −78° for a further ten minutes, and then it was allowed to warm to room temperature before being neutralised with acetic acid. The solvent was evaporated under reduced pressure, the residue chromatographed on silica gel 60 (<230 mesh), eluting with ethyl acetate/60°-80° petroleum ether mixtures grading from 1:1 to 3:1. This gave a mixture of the cis and trans isomers of 4-allyl-1-(1-benzyloxycarbonyl-1-triphenylphosphoranylidene methyl)-3-(1-hydroxy-1-phenylmethyl)azetidin-2-one (1.52 g, 63%) (26) and (27) ν$_{max}$ (CHCl₃) 3400, 3000, 1725, 1615 cm⁻¹.

(ii) Benzyl 6-(1-hydroxy-1-phenylmethyl)-7-oxo-1-azabicyclo[3,2,0]hept-2-ene-2-carboxylate

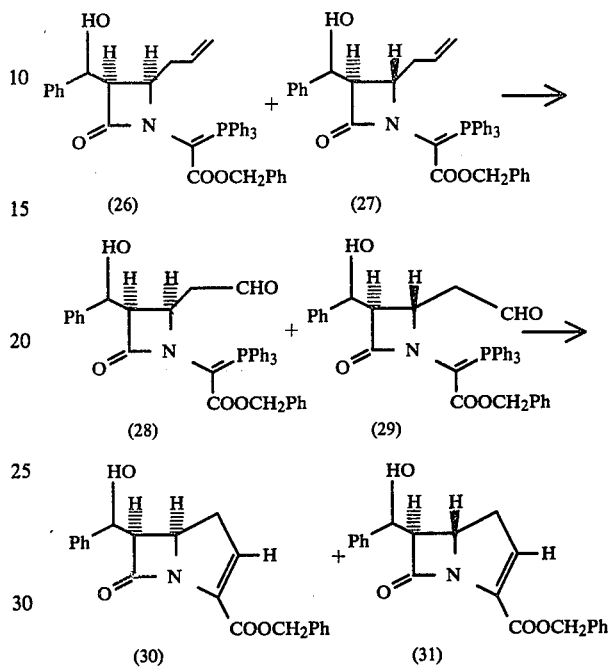

A mixture of cis and trans-isomers of 4-allyl-1-(1-benzyloxycarbonyl-1-triphenylphosphoranylidenemethyl)-3-(1-hydroxy-1-phenylmethyl)azetidin-2-one (0.80 g) as obtained in section (i) was dissolved in ethyl acetate (40 ml). An excess of trifluoroacetic acid (1.50 g) was added and the mixture cooled to −78°. Ozone was passed into the reaction mixture until it was pale blue in colour. Argon was then bubbled through the solution until all the excess ozone had been removed. A solution of triphenylphosphine (0.34 g) in ethyl acetate was added and argon bubbled through the mixture for a further ten minutes. The reaction flask was allowed to warm to room temperature, and a saturated solution of sodium bicarbonate (20 ml) was added to generate the phosphoranes (28) and (29). Argon was passed through the mixture for thirty minutes. The ethyl acetate layer was separated, washed with brine, and dried over sodium sulphate.

The solution was left to stand at room temperature for three days to allow the cyclisation reactions to proceed to completion. The ethyl acetate layer was evaporated off under reduced pressure and the residue chromatographed on silica gel 60 (<230 mesh), eluting with 1:1 ethyl acetate/cyclohexane. Only two of the four possible diastereoisomers of benzyl 6-(1-hydroxy-1-phenylmethyl)-7-oxo-1-azabicyclo[3,2,0]hept-2-ene-2-carboxylate could be isolated from the reaction mixture; these were one cis and one trans isomer about the β-lactam ring. The pure cis-isomer (30) (0.12 g 27%) was a crystalline material which could be recrystallized from ethyl acetate/60°-80° petroleum ether; m.p. 124°; ν$_{max}$ (CHCl₃) 3550, 3010, 1775, 1725 and 1610 cm⁻¹; δ ppm (C₆D₆) 1.5-1.9 (1H, m, C4-H) 2.2-2.7 (2H, m, C4-H and OH), 3.2-3.7 (2H, m, C5-H and C6-H), 4.43 (1H, dd, J 7 and 3 Hz, CH-O)), 5.09 and 5.11 (2H, centre lines of ABq, benzyl CH$_2$), 6.12 (1H, t, J 3 Hz, C3-H) and 7.0-7.4 (10H, m, phenyls); $\lambda_{max}$ (EtOH) 277 nm ($\epsilon$ 4830).

The pure trans-isomer (31) (0.12 g, 27%) had $\nu_{max}$ (CHCl$_3$) 3600-3400, 3020, 1775, 1715 and 1610 cm$^{-1}$, $\delta$ ppm (C$_6$D$_6$) 1.89 (2H, dd, J 9 and 3 Hz, C4-H$_2$), 2.70 (1H, br, OH), 3.15 (1H, dd, J 5 and 3 Hz, C6-H), 3.69 (1H, td, J9 and 3 Hz, C5-H), 4.67 (1H, d, J 5 Hz, CH-O), 5.01 and 5.03 (2H, centre lines of ABq, benzyl CH$_2$), 5.90 (1H, t, J 3 Hz, C3-H) and 6.9-7.4 (10H, m, phenyls).

The $\beta$-lactamase inhibition (I$_{50}$) values in $\mu$g/ml for (30) were as follows:
Proteus mirabilis C889: 0.27
Staphylococcus aureus Russell: 0.052

EXAMPLE 7

Benzyl 6-(1-hydroxycyclohex-1-yl)-7-oxo-1-azabicyclo[3,2,0-]hept-2-ene-2-carboxylate

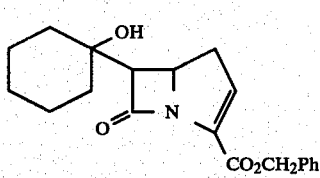

(i) 4-Allyl-1-(1-benzyloxycarbonyl-1-triphenylphosphoranylidenemethyl)-3-(1-hydroxycyclohex-1-yl)azetidin-2-one

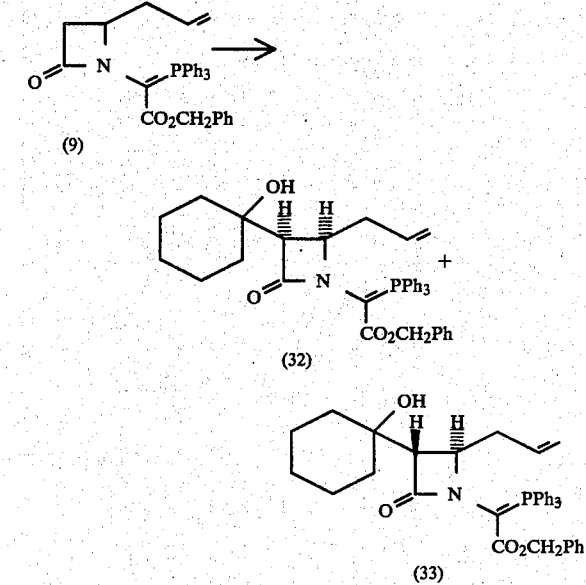

A solution of N-isopropylcyclohexylamine (0.60 g) in dry tetrahydrofuran (5 ml) was cooled to −78° and stirred under an argon atmosphere. It was treated with a 1.6 M solution of n-butyl lithium in hexane (2.7 ml) and after 10 minutes a solution of 4-allyl-1-(1-benzyloxycarbonyl-1-triphenylphosphoranylidenemethyl)azetidine-2-one (9) (1.00 g) in dry tetrahydrofuran (15 ml) was added. The resulting red-brown solution was stirred for a further 10 minutes and then treated with cyclohexanone (0.40 ml). The reaction mixture was allowed to warm to about 0° to allow the reaction to go to completion; at which point the solution became pale yellow. It was neutralized with acetic acid (0.56 g.) and the solvent evaporated off under reduced pressure. The residue was partitioned between ethyl acetate and brine. The ethyl acetate solution was separated, dried over sodium sulphate and then concentrated. The residue was chromatographed on silica gel 60 (<230 mesh) eluting with ethyl acetate/60°-80° petroleum ether 1:1 grading to 7:3. This yielded a mixture of cis and trans-isomers of 4-allyl-1-(1-benzyloxycarbonyl-1-triphenylphosphoranylidenemethyl)-3-(1-hydroxycyclohex-1-yl)azetidine-2-one (32) and (33) (0.76 g, 64%); $\nu_{max}$ (CHCl$_3$) 3400, 2980, 2920, 2850, 1735 and 1615 cm$^{-1}$.

(ii) Benzyl 6-(1-hydroxycyclohex-1-yl)-7-oxo-1-azabicyclo[3,2,0]hept-2-ene-2-carboxylate

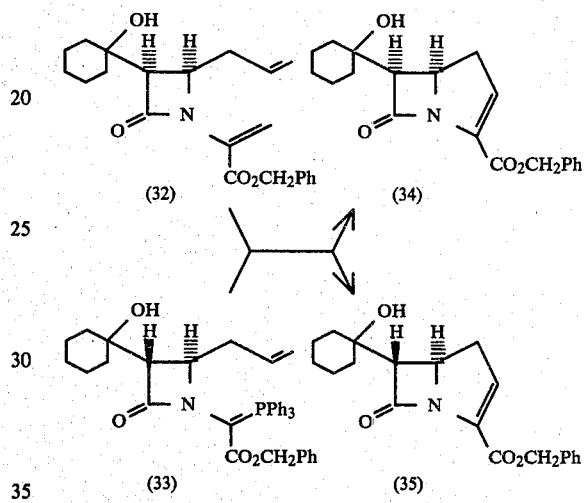

A solution of the mixed isomers of 4-allyl-1-(1-benzyloxycarbonyl-1-triphenylphosphoranylidenemethyl)-3-(1-hydroxycyclohex-1-yl)azetidin-2-one (32) and (33) (0.75 g.) in ethyl acetate (50 ml) was treated with trifluoroacetic acid (2.0 ml). The solution was cooled to −78° and ozone passed through until the solution just became blue. The excess ozone was blown off in a stream of argon and a solution of triphenylphosphine (0.32 g) in ethyl acetate (5 ml) added. The passage of argon through the solution was continued for 30 minutes and then the reaction flask was transferred to an ice bath. Saturated aqueous sodium bicarbonate (60 ml) was added in one portion with vigorous stirring, to neutralize the reaction. After a further 30 mins. the ethyl acetate solution was separated, washed with brine, and dried over sodium sulphate. It was set aside overnight and the solution was then concentrated and chromatographed on silica gel 60 (<230 mesh) eluting with ethyl acetate/60°-80° petroleum ether 3:7 grading to 1:1. The first $\beta$-lactam containing compound to be eluted with the cis-isomer of benzyl 6-(1-hydroxycyclohex-1-yl)-7-oxo-1-azabicyclo[3,2,0]hept-2-ene-2-carboxylate (34) (0.04 g, 10%); m.p. 125°-126° (ethyl acetate/60°-80° petroleum ether); $\nu_{max}$ (CHCl$_3$) 3600, 3000, 2920, 2850, 1770, 1720 and 1615 cm$^{-1}$. $\lambda_{max}$ (EtOH) 275 nm ($\epsilon$ 4240); $\tau$ (CDCl$_3$) 2.6-2.8 (5H, m, phenyl), 3.50 (1H, t, J 3 Hz, C3-H), 4.73 and 4.89 (2H, AB1, J 12 Hz, benzyl CH$_2$), 5.76 (1H, td, J 9 and 5½ Hz, C5-H), 6.24 (1H, ddd, J 18, 9 and 3 Hz, C4-H), 6.39 (1H, d, J 5½ Hz, C6-H), 7.42 (1H, ddd, J 18, 9 and 3 Hz, C4-H), 8.36 (1H, s, OH) and 8.1-8.8 (10H, m, cyclohexyl); (Found: C, 70.4; H, 6.8; N, 4.1%. $C_{20}H_{23}NO_4$ requires C, 70.4; H, 6.8 and N, 4.1%).

Further elution of the column gave the corresponding trans-isomer (35) (0.18 g. 43%); m.p. 102°-4° (ethyl acetate/60°-80° petroleum ether); $\nu_{max}$ (CHCl$_3$) 3550, 3000, 2920, 2850, 1775, 1725 and 1615 cm$^{-1}$; $\lambda_{max}$ (EtOH) 279 nm ($\epsilon$ 4530); $\tau$ (CDCl$_3$) 2.6-2.8 (5H, m, phenyl), 3.61 (1H, t, J 2½ Hz, C3-H), 4.71 and 4.87 (2H, ABq, J 12 Hz, benzyl CH$_2$), 5.76 (1H, td, J 8 and 3 Hz, C5-H), 6.78 (1H, d, J 3 Hz, C6-H), 7.09 (1H, ddd, J 18, 8 and 2½ Hz, C4-H), 7.34 (1H, ddd, J 18, 8 and 2½ Hz, C4-H), 8.25 (1H, s, OH) and 8.1-8.8 (10H, m, cyclohexyl); (Found: C, 70.4; H, 6.7; N, 4.0%. $C_{20}H_{23}NO_4$ requires C, 70.4; H, 6.8 and N, 4.1%).

The β-lactamase inhibition (I$_{50}$) values in µg/ml for (34) were as follows:
Enterobacter P99: 5
*Pseudomonas aeruginosa* A: 1.4
*Escherichia coli* JT 4: 16
*Staph. aureus* Russell: 4.6

EXAMPLE 8

Benzyl 6-benzyl-7-oxo-1-azabicyclo[3,2,0]hept-2-ene-2-carboxylate

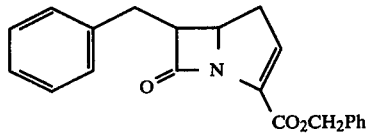

(i)
4-Allyl-3-benzyl-1-(1-benzyloxycarbonyl-1-triphenylphosphoranylidenemethyl)azetidine-2-one

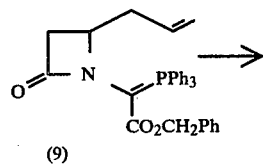

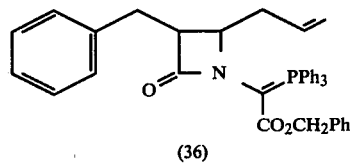

A solution of N-isopropylcyclohexylamine (0.60 g) in dry tetrahydrofuran (5 ml) was stirred under argon and cooled to −78°. It was treated with a 1.6 M solution of n-butyl lithium in hexane (3.0 ml) and after 10 mins a solution of 4-allyl-1-(1-benzyloxycarbonyl-1-triphenylphosphoranylidenemethyl)azetidine-2-one (9) (1.00 g) in dry tetrahydrofuran (12 ml) was added to give a red solution. After a further 10 minutes the reaction mixture was treated with benzyl bromide (0.36 g) and 5 minutes later the reaction flask was removed from the cooling bath to allow the reaction to go to completion. It was neutralized with acetic acid (ca 0.5 g.) and then concentrated. Column chromatography on silica gel 60 (<230 mesh) eluting with ethyl acetate/60°-80° petroleum ether 1:1 grading to 7:3 gave 4-allyl-3-benzyl-1-(1-benzyloxycarbonyl-1-triphenylphorphoranylidenemethyl)azetidine-2-one (36) (0.38 g, 32%); $\nu_{max}$ (CHCl$_3$) 2980, 1730 and 1610 cm$^{-1}$. Continued elution resulted in recovery of the starting phosphorane (9) (0.42 g, 42%).

(ii) Benzyl 6-benzyl-7-oxo-1-azabicyclo[3,2,0]hept-2-ene-2-carboxylate

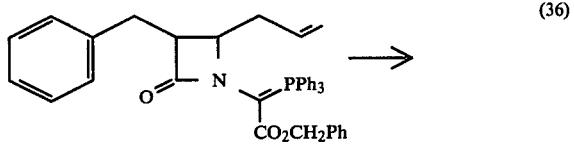

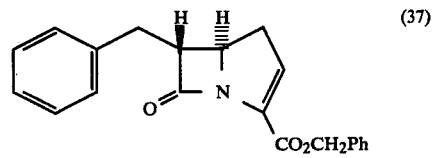

A solution of 4-allyl-3-benzyl-1-(1-benzyloxycarbonyl-1-triphenylphosphoranylidenemethyl)azetidine-2-one (36) (0.38 g) in ethyl acetate (20 ml) was treated with trifluoroacetic acid (1.0 ml). The solution was cooled to −78° and ozone passed through it until it just became blue in colour. The excess ozone was blown off in a stream of argon and a solution of triphenylphosphine (0.16 g) in ethyl acetate (2 ml) was then added. The reaction solution was purged with argon for the next 30 minutes and the reaction flask was then transferred to an ice bath. Saturated aqueous sodium bicarbonate (30 ml) was added with vigorous stirring and after a further 30 minutes the ethyl acetate solution was separated, washed with brine and dried over sodium sulphate. Column chromatography on silica gel 60 (<230 mesh) eluting with ethyl acetate/60°-80° petroleum ether 3:7 gave benzyl 6-benzyl-7-oxo-1-azabicyclo[3,2,0]hept-2-ene-2-carboxylate as the trans isomer (37) (0.09 g. 42%). It was a colourless gum; $\nu_{max}$ (CHCl$_3$) 3020, 2960, 1785, 1725 and 1610 cm$^{-1}$; $\tau$ (CDCl$_3$) 2.6-3.0 (10H, m, phenyls), 3.66 (1H, t, J 3 Hz, C3-H), 4.80 (2H, s, benzyl CH$_2$-O), 6.02 (1H, td, J 8½ and 3 Hz, C5-H), 6.60 (1H, ddd, J 9, 6 and 3 Hz, C6-H), 6.88 (1H, d, J 6 Hz, inner signal of ABX for PhCH$_2$-C6), 6.97 (1H, d, J 9 Hz, inner signal of ABX for PhCH$_2$-C6), 7.29 and 7.32 (2H, each a dd, J 8½ and 3 Hz, inner signals of AB for C4-H$_2$).

EXAMPLE 9

Benzyl 6-methyl-7-oxo-1-azabicyclo[3,2,0]hept-2-ene-2-carboxylate (i)
4-Allyl-3-methyl-1-(1-benzyloxycarbonyl-1-triphenyl-phosphoranylidenemethyl)azetidine-2-one

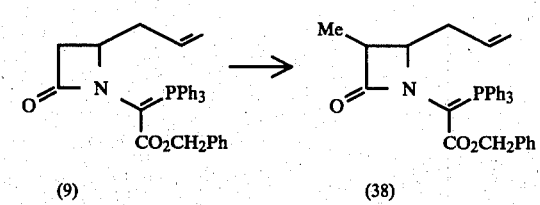

A solution of N-isopropylcyclohexylamine (0.30 g) in dry tetrahydrofuran (5 ml) was stirred under argon and cooled to −78°. This was treated with a 2.5 M solution of n-butyl lithium in hexane (0.85 ml) and stirred for 10 minutes. A solution of 4-allyl-1-(1-benzyloxycarbonyl-1-triphenylphosphoranylidenemethyl)azetidine-2-one (9) (0.50 g) in tetrahydrofuran (5 ml) was added and after 5 minutes the anion was quenched by addition of methyl iodide (0.12 ml). After a period of 10 minutes the reaction vessel was transferred to an ice bath and a further 10 minutes later the reaction was neutralized by addition of acetic acid (0.16 ml). The solvent was then stripped off and the residue partitioned between ethyl acetate and brine. The ethyl acetate solution was separated, washed with brine and dried over sodium sulphate. The product was subjected to careful column chromatography on silica gel 60 eluting with cyclohexane/ethyl acetate mixtures grading from 1:1 to 3:7. This gave 4-allyl-3-methyl-1-(1-benzyloxycarbonyl-1-triphenylphosphoranylidenemethyl)azetidine-2-one (38) (0.10 g, 19%); $\nu_{max}$(CHCl$_3$) 3000, 1735 and 1610 cm$^{-1}$. Running closely behind this was recovered starting phosphorane (9) (0.17 g, 33%).

(ii) Benzyl 6-methyl-7-oxo-1-azabicyclo[3,2,0]hept-2-ene-2-carboxylate

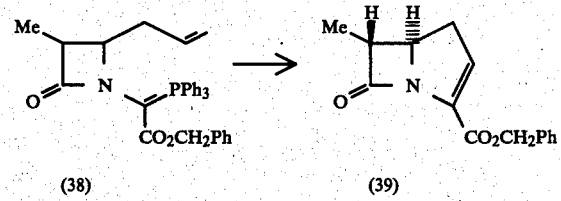

A solution of 4-allyl-3-methyl-1-(1-benzyloxycarbonyl-1-triphenylphosphoranylidenemethyl)azetidine-2-one (38) (0.29 g) in ethyl acetate (25 ml) was treated with trifluoroacetic acid (0.4 ml) and then cooled to −78°. Ozone was bubbled through the solution until it just became pale blue in colour. The excess ozone was blown off in a stream of argon and an ethyl acetate solution of triphenylphosphine (0.14 g) was then added. After a further 10 minutes the reaction flask was transferred to an ice bath and saturated aqueous sodium bicarbonate (45 ml) was added with vigorous stirring. This was continued for 30 minutes and the ethyl acetate solution was then separated, washed with brine and dried over sodium sulphate. The solution was concentrated and chromatographed on silica gel 60 (<230 mesh) eluting with ethyl acetate/60°-80° petroleum ether mixtures grading from 3:7 to 6:4. This gave the trans-isomer of benzyl 6-methyl-7-oxo-1-azabicyclo[3,2,0]hept-2-ene-2-carboxylate (39) (0.08 g, 55%);

$\nu_{max}$ (CHCl$_3$) 3000, 1780, 1725 and 1615 cm$^{-1}$; δ ppm ((CD$_3$)$_2$CO) 1.34 (3H, d, J 7 Hz, CH$_3$), 2.85 (2H, dd, J 9 and 2 Hz, C4-H$_2$), 3.24 (1H, dq, J 3 and 7 Hz, C6-H), 3.91 (1H, dt, J 3 and 9 Hz, C5-H), 5.20 (2lH, s, benzyl CH$_2$), 6.45 (1H, t, J 2 Hz, C3-H) and 7.2–7.5 (5H, m, phenyl); (M$^+$ at m/e 257.1052 C$_{15}$H$_{15}$NO$_3$ requires 257.1051).

EXAMPLE 10

Phthalidyl 6-(3-methoxycarbonyl-2-propen-1-yl)-7-oxo-1-azabicyclo[3,2,0]hept-2-ene-2-carboxylate

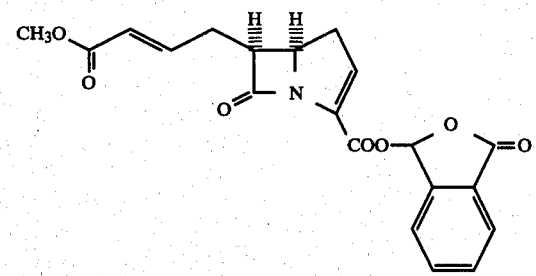

(i) Preparation of 7-(1-phthalidyloxycarbonyl-1-triphenylphosphoranylidenemethyl)-8-oxo-7-azabicyclo[4,2,0]oct-3-ene

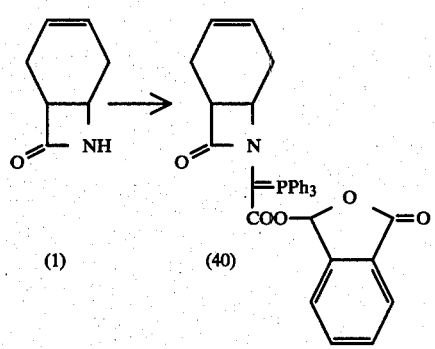

The azetidinone (1) (0.6 g), glyoxylic acid monohydrate (0.46 g), 4×4A° molecular sieves (⅛" pellets), and dry DMF (3 ml) were stirred at room temperature for 5 hours. The mixture was cooled to 0° and potassium carbonate (0.345 g) was added. The mixture was allowed to warm up to room temperature and stirred for 5 minutes. Bromophthalide (1.07 g) was added and the mixture was stirred for 16 hours. The resulting solution was poured onto N/10 hydrochloric acid (25 ml) and ethyl acetate (25 ml). The organic layer was washed once more with N/10 hydrochloric acid (25 ml) and then with saturated aqueous sodium hydrogen carbonate (25 ml) and brine (25 ml); each aqueous washing being extracted once with ethyl acetate (25 ml). The combined organic layers were dried (Na$_2$SO$_4$) and the solvent removed under reduced pressure to give a white solid (0.73 g).

A stirred solution of this solid in dry tetrahydrofuran (30 ml), under argon, was cooled to −20°, and treated with 2,6-lutidine (0.52 ml) followed by thionyl chloride (0.33 ml) in tetrahydrofuran (2 ml). After stirring for 20 minutes at −20 the mixture was brought to room temperature and filtered. The precipitated solid was washed with toluene and the combined flitrate and washings were evaporated to dryness under reduced pressure. The residue was dissolved in toluene and re-evaporated to dryness to remove excess thionyl chloride.

The oil obtained was dissolved in dry tetrahydrofuran (25 ml) and treated with 2,6-lutidine (0.52 ml) and triphenylphosphine (1.2 g). After stirring for 16 hours, the mixture was filtered and the filtrant washed with ethyl acetate (25 ml). The filtrate and washings were combined and the solvent removed under reduced pressure. The residue was dissolved in ethyl acetate (50 ml) and N/2 hydrochloric acid (25 ml). The organic layer was separated and the aqueous layer washed once with ethyl acetate (25 ml). The combined organic extracts were dried ($Na_2SO_4$) and the solvent removed.

Chromatography on silica gel eluting with petroleum ether/ethyl acetate mixtures gave the phosphorane (40) which crystallised on addition of ether (0.9 g) m.p. 143°-5° (ethyl acetate/petroleum ether) having $\nu_{max}$ ($CHCl_3$) 1780, 1740, 1670 sh, and 1640 cm$^{-1}$. (Found: C, 73.4; H, 5.0; N, 2.3. $C_{35}H_{28}NPO_5$ requires C, 73.3; H, 4.9; N, 2.4%).

(ii) Preparation of Phthalidyl 6-(3-methoxycarbonyl-2-propen-1-yl)-7-oxo-1-azabicyclo[3,2,0]hept-2-ene-2-carboxylate

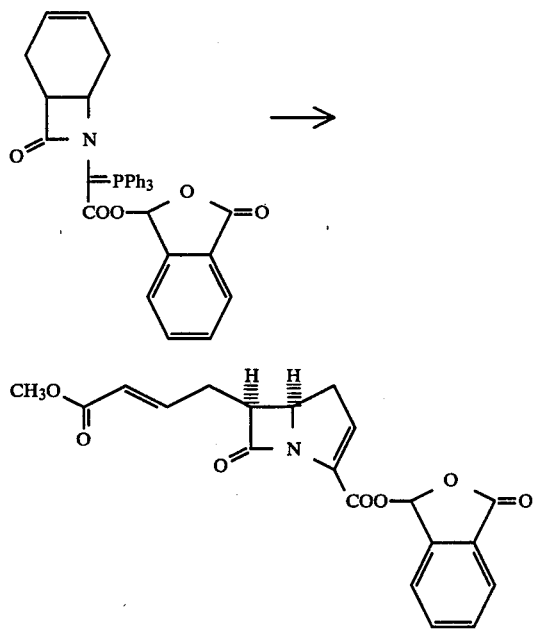

The phosphorane (40) (0.345 g) was dissolved in 5:1 ethyl acetate/trifluoroacetic acid (15 ml). The solution was left at room temperature for 10 minutes and then cooled to −70°. Ozone was then passed through the solution until it became pale blue. Argon was passed through the solution to remove excess ozone and then triphenylphosphine (0.2 g) in ethyl acetate (2 ml) was added. The mixture was warmed up to 0° with an ice bath and then saturated sodium hydrogen carbonate solution (50 ml) was added carefully with vigorous agitation. The layers were separated and the aqueous layer extracted once more with ethyl acetate (25 ml). The combined organic layers were dried ($Na_2SO_4$), filtered and allowed to stand at room temperature for 3 hours. Methoxycarbonylmethylenetriphenylphosphorane (0.21 g) was added to the solution dissolved in ethyl acetate and left for 1 hour. The solution was evaporated to dryness. Rapid chromatography on silica/hyflo eluting with 1:1 ethyl acetate/petroleum ether followed by slower chromatography on silica gel eluting with 1:1 ethyl acetate/petroleum ether gave the phthalide ester (41) (0.084 g) as a white solid. m.p. 140.5° (ethyl acetate/petroleum ether) having $\nu_{max}$ ($CHCl_3$) 1795, 1745, 1725, 1665, 1615 and 980 cm$^{-1}$. δ ($CDCl_3$) 2.4–2.9 (4H, m, methylenes), 3.70 (3H, s, $CH_3$), 3.6–3.9 (1H, m, C4-H), 4.4 (1H, m, C5-H), 5.8 (1H, br.d, J 16 Hz, $MeO_2C$—CH=), 6.50 and 6.62 (1H, 2×t, J 3 Hz, C3-H in two isomers), 6.85 (1H, dt, J 6, 16 Hz, $MeO_2CCH$=CH—), 7.41 and 7.47 (1H, 2×s, phthalide methines), and 7.55–7.95 (4H, m, aromatic), $\lambda_{max}$ (EtOH) 208, 274 (δ 6,900), and 280 (δ 6,700) nm. (Found: C, 62.0; H, 4.4; N, 3.6. $C_{20}H_{17}NO_7$. ¼ $H_2O$ requires C, 62.0; H, 4.5; N, 3.6%).

The concentrations of this compound required to inhibit the growth of the following bacteria are given below.

| Organism | μg/ml (agar) |
|---|---|
| *B. subtilis* A | 25 |
| *E. coli* 0111 | 50 |
| *Klebsiella aerogenes* A | 50 |
| *Proteus mirabilis* C977 | 100 |
| *Salmonella typhimurium* CT 10 | 50 |
| *Shigella sonnei* MB 11967 | 50 |
| *Staph. aureus* Oxford | ≦0.8 |
| *Staph. aereus* Russell | ≦0.8 |
| *Staph. aureus* 1517 | ≦0.8 |
| *Strep. pyogenes* CN 10 | ≦0.8 |

EXAMPLE 11

Phthalimidomethyl 6-(3-methoxycarbonyl-2-propen-1-yl)-7-oxo-1-azabicyclo [3,2,0]hept-2-ene-2-carboxylate

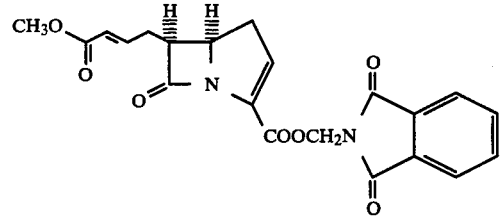

(i) Preparation of 7-(1-Hydroxy-1-phthalimidomethoxycarbonylmethyl)-8-oxo-7-azabicyclo[4,2,0]oct-3-ene

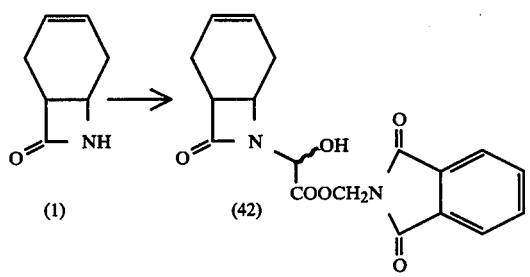

The azetidinone (1) (0.6 g), glyoxylic acid monohydrate (0.48 g), 6×4A° molecular sieves (⅛" pellets), and dry DMF (3 ml) were stirred at room temperature for 5 hours. Potassium carbonate (0.365 g) was added followed by phthalimidomethyl bromide (1.25 g) and the mixture was stirred for 16 hours. The resulting solution was poured onto ethyl acetate (25 ml) and N/10 hydrochloric acid (25 ml). The organic layer was washed with saturated sodium hydrogen carbonate (25 ml) and brine, each aqueous washing being extracted once with ethyl acetate (25 ml). Drying (MgSO₄) and removal of solvent from the combined extracts followed by chromatography on silica gel (eluted with ethyl acetate/petroleum ether mixtures) gave the alcohols (42) (0.91 g) as a white solid. The alcohols can be separated by more careful chromatography. Isomer I m.p. 132-4 (ethyl acetate/petroleum ether) has $\nu_{max}$ (CHCl₃) 1790, 1735, 1670 and 1390 cm⁻¹, δ (CDCl₃) 1.85-2.75 (4H, m, allylic CH₂) 3.27 (1H, m, β-lactam H), 4.05 (1H, m, β-lactam H), 4.37 (1H, d, J 7 Hz, OH), 5.38 (1H, d, J 7 Hz, CHOH), 5.77 (4H, m, olefinic and —CH₂—N), and 7.76 (4H, m, aromatic). (Found: C, 60.5; H, 4.75; N, 7.75. $C_{18}H_{16}N_2O_6$ requires C, 60.7; H, 4.5; N, 7.85%), and Isomer II m.p. 145 (ethyl acetate/petroleum ether) has δ (CDCl₃) 1.85-2.6 (4H, m, allylic CH₂) 3.29 (1H, m, β-lactam H), 4.14 (1H, m, β-lactam H), 4.71 (1H, br, OH), 5.36 (1H, br, CH-OH), 5.67 (2H, m, olefinic), 5.73 (2H, s, —CH₂—N), and 7.77 (4H, m, aromatic). (Found: C, 60.8; H, 4.20; N, 7.75. $C_{18}H_{16}N_2O_6$ requires C, 60.7; H, 4.5; N, 7.85%).

(ii) Preparation of 7-(1-Phthalimidomethoxycarbonyl-1-triphenylphosphoranylidenemethyl)-8-oxo-7-azabicyclo[4,2,0]oct-3-ene

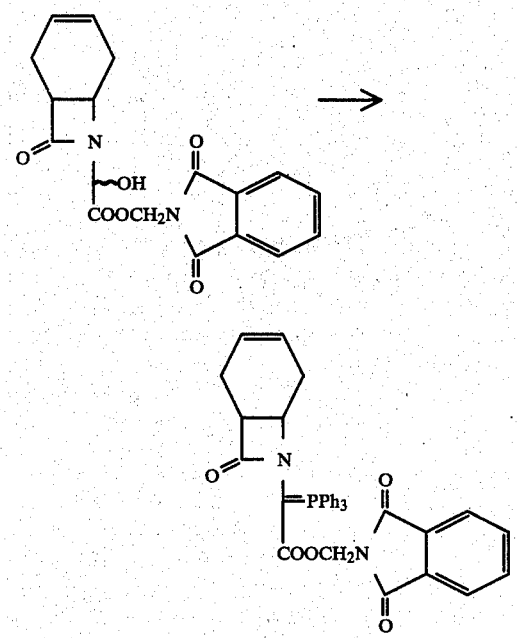

A stirred solution of the alcohols (42) (0.91 g) in dry tetrahydrofuran (20 ml) under argon, was cooled to −20°, and treated with 2,6-lutidine (0.59 ml) followed by thionyl chloride (0.366 ml) in tetrahydrofuran (3 ml). After stirring for 20 minutes at −20° the mixture was brought to room temperature and filtered. The precipitated solid was washed with toluene and the combined filtrate and washings were evaporated to dryness. The residue was dissolved in toluene and re-evaporated to remove the thionyl chloride.

The oil obtained was dissolved in dry tetrahydrofuran (20 ml) and treated with 2,6-lutidine (0.59 ml) and triphenylphosphine (1.33 g). After stirring for 16 hours, the mixture was filtered and the solvent removed from the filtrate. Chromatography on silica gel eluting with petroleum ether/ethyl acetate gave the phosphorane (43), which crystallised on addition of ether; (1.23 g), having $\nu_{max}$ (CHCl₃) 1790, 1735 and 1625 cm⁻¹.

(iii) Preparation of Phthalimidomethyl 6-(3-methoxycarbonyl-2-propen-1-yl)-7-oxo-1-azabicyclo[3,2,0]hept-2-ene-2l-carboxylate

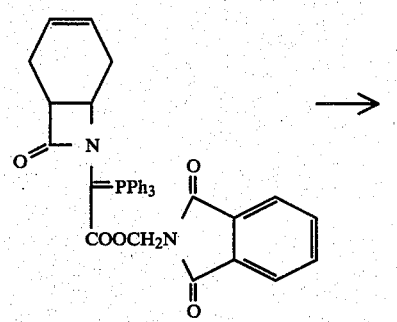

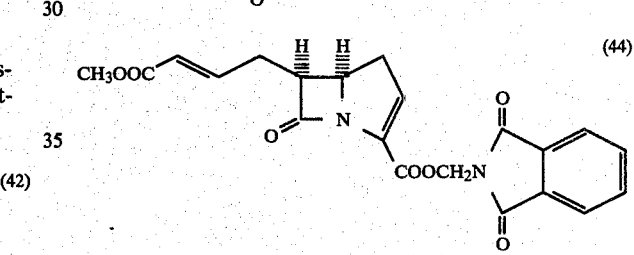

The phosphorane (43) (0.24 g) was dissolved in ethyl acetate (10 ml) and trifluoroacetic acid (0.32 ml) was added. The reaction mixture was cooled to −70° and ozone was bubbled in until the solution became pale blue. Argon was passed through the solution to remove excess ozone and then triphenylphosphine (0.16 g) in ethyl acetate (2 ml) was added. The mixture was warmed up to 0° with an ice bath and then saturated sodium hydrogen carbonate (10 ml) was added with vigorous agitation. After 1 hour at room temperature, the layers were separated and methoxycarbonylmethylenetriphenylphosphorane (0.14 g) was added to the ethyl acetate layer. After one hour the solvent was removed and the resulting oil initially purified by chromatography on silica eluted with petroleum ether/ethyl acetate. Further purification using a thick silica plate eluted with ethyl acetate gave the ester (44) (0.05 g) as a white solid m.p. 132-137 having $\nu_{max}$ (CHCl₃) 1790, 1740, 1660 and 1620 cm⁻¹. δ (CDCl₃) 2.4-2.8 (4H, m, methylenes), 3.5-3.85 (1H, m, C6-H), 3.7 (3H, s, CH₃), 4.35 (1H, dt, J 6, 9 Hz, C5-H), 5.65-5.95 (3H, m, MeO₂CCH= and OCH₂N), 6.46 (1H, t, J 3 Hz, C3-H), 6.83 (1H, dt, J 7, 16 Hz, MeO₂CCH=CH—), and 7.6-7.95 (4H, m, aromatic). (Found: C, 60.1; H,4.5; N, 6.65. $C_{21}H_{18}N_2O_7 \cdot \frac{1}{2}H_2O$ requires C, 60.1; H, 4.55; N, 6.70%).

EXAMPLE 12

Phthalidyl 6-(2-oxoethyl)-7-oxo-1-azabicyclo[3,2,0]hept-2-ene-2-carboxylate

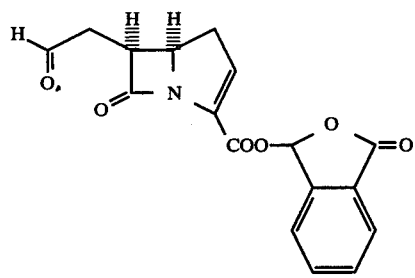

(i) Preparation of 7-(1-phthalidyloxycarbonyl-1-tris-p-methoxyphenyl-phosphoranylidenemethyl)-8-oxo-7-azabicyclo[4,2,0]oct-3-ene

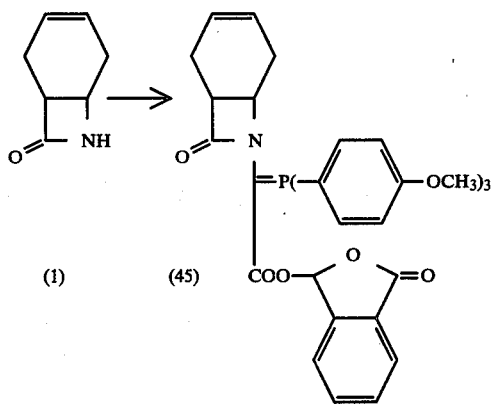

The phosphorane (45) was prepared as in Example 10 (i) except that tris-p-methoxyphenylphosphine (1.2 g) was used instead of triphenylphosphine. Chromatography gave the phosphorane (45) (0.71 g) m.p. 194–6 (ethyl acetate/petroleum ether) having $v_{max}$ (CHCl$_3$) 1780, 1745, 1650, 1600, 1265 and 1115 cm$^{-1}$ (Found: C, 67.35; H, 5.0; N, 1.8. C$_{38}$H$_{34}$PNO$_8$.H$_2$O requires C, 66.95; H, 5.3; N, 2.0%).

(ii) Preparation of 6-(2-oxoethyl)-7-oxo-1-azabicyclo[3,2,0]hept-2-ene-2-carboxylate

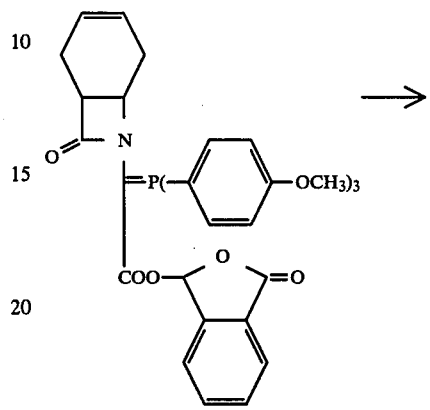

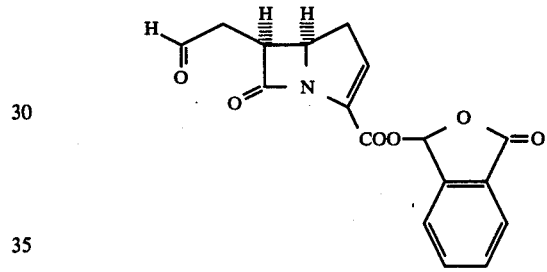

The phosphorane (45) (0.133 g) was dissolved in 5:1 ethyl acetate/trifluoroacetic acid (6 ml). The solution was left at room temperature for 10 minutes and then cooled to −70°. Ozone was then passed through the solution until it became pale blue and excess ozone removed with argon. Tris-p-methoxyphenylphosphine (0.07 g) in ethyl acetate (1 ml) was added and the solution was warmed up to 0° with an ice bath. Saturated aqueous potassium hydrogen carbonate (5 ml) was added carefully with vigorous agitation and the layers were separated. The aqueous layer was washed twice with ethyl acetate (5 ml) and the combined organic layers dried (MgSO$_4$). This solution was heated at 45° for ¾ hour and then the solvent was removed under reduced pressure. Rapid chromatography on silica eluting with 1:1 petroleum ether/ethyl acetate gave the aldehyde (46) (0.02 g) as a white solid after trituration with ether having $v_{max}$ (CHCl$_3$) 2950, 1795, 1740, 1610 and 980 cm$^{-1}$ and n.m.r. having δ 9.17 (s, aldehyde C-H).

EXAMPLE 13

Phthalidyl 6-(4l-oxo-2-penten-1-yl)-7-oxo-1-azabicyclo[3,2,0]hept-2-ene-2-carboxylate

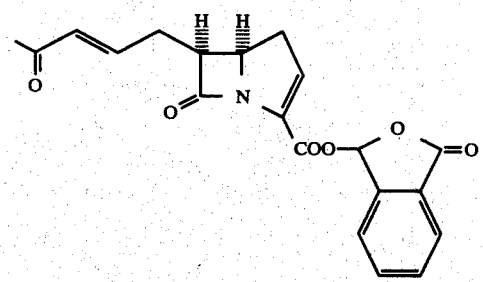

(i) Preparation of Acetonyltris-p-methoxyphenylphosphonium chloride

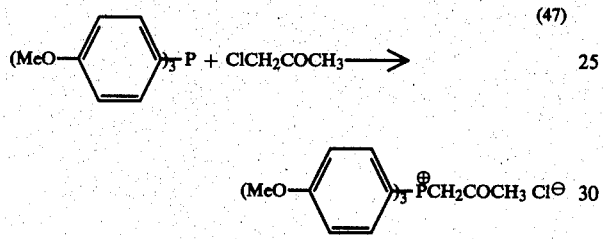
(47)

A solution of tris-p-methoxyphenylphosphine (2.66 g) and chloroacetone (0.65 g) in chloroform (6 ml) was heated under reflux for 45 minutes. The solution was poured into ether (60 ml) and the solid collected. The chloride (47) had $v_{max}$(KBr) 2800, 1710, 1595, and 1270 cm$^{-1}$. $\lambda_{max}$(EtOH) 212 ($\epsilon$ 37,100) and 247 ($\epsilon$ 45,800)nm, $\delta$ (CDCl$_3$) 2.48 (3H, d, J 2 Hz, COCH$_3$), 3.88 (9H, s, OCH$_3$), 5.77 (2H, d, J 11 Hz, CH$_2$), and 6.95–8.0 (12H, m, aromatic).

(ii) Preparation of Acetylmethylenetris-p-methoxyphenylphosphorane

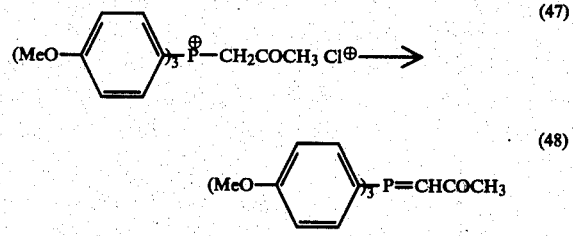
(48)

Sodium carbonate (0.053 g) in water (5 ml) was added to a suspension of the chloride (47) (0.445 g) in benzene (5 ml). After stirring for 5 minutes, the organic layer was separated, dried (MgSO$_4$) and the benzene was removed under reduced pressure. The resulting oil crystallised from ether/cyclohexane and had m.p. 148.5-149 (ethyl acetate/petroleum ether), $\delta$ (CDCl$_3$) 2.07 (3H, d, J 2 Hz, COCH$_3$), 3.83 (10H, s, obscuring br.s, =CH and OCH$_3$) and 6.85-7.75 (12H, m, aromatics)(Found: C, 70.44; H, 6.25; C$_{24}$H$_{25}$PO$_4$ requires C, 70.59; H, 6.15%).

(iii) Preparation of Phthalidyl 6-(4-oxo-2-penten-1-yl)-7-oxo-1-azabicyclo[3,2,0]hept-2-ene-2-carboxylate

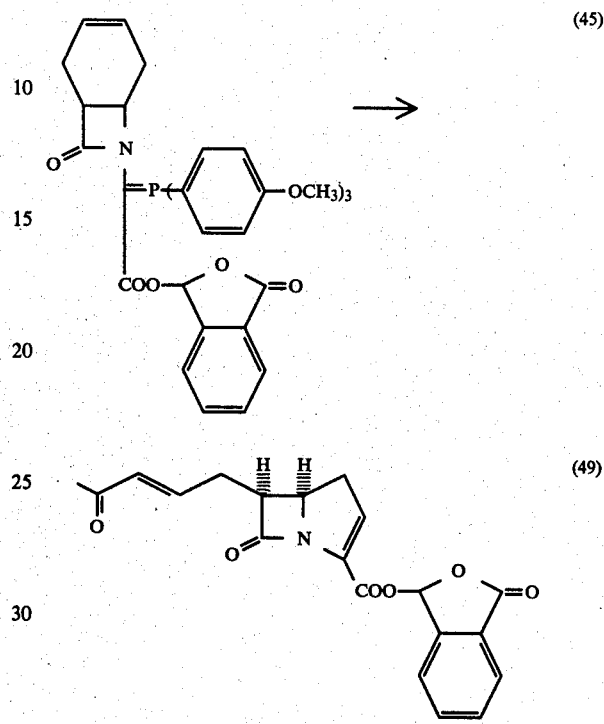

The phosphorane (45) (0.4 g) [as prepared in Example 12(i)] was dissolved in 5:1 ethyl acetate - trifluoroacetic acid (18 ml). The solution was left at room temperature for 10 minutes and then cooled to −70°. Ozone was then passed through the solution until it became pale blue. Argon was passed through the solution to remove excess ozone and then tris-p-methoxyphenylphosphine (0.2 g) in ethyl acetate (2 ml) was added. The mixture was warmed up to 0° with an ice bath and then saturated potassium hydrogen carbonate (15 ml) was added carefully with vigorous agitation. The layers were separated and the aqueous layer extracted twice more with ethyl acetate (25 ml). The combined organic layers were dried (MgSO$_4$), filtered and then heated for 15 minutes at 50°. Acetylmethylenetris-p-methoxyphenylphosphorane (0.2 g) was added, and the solution heated at 50° for 1½ hour and then left overnight at room temperature. Chromatography on silica eluting with ethyl acetate - petroleum ether mixtures gave the ketone (49)(0.015 g) as an oil having $v_{max}$(CHCl$_3$) 1795, 1750, 1680, 1635, 1615 and 985 cm$^{-1}$, $\delta$ (CDCl$_3$) 1.8-3.0 (4H, m, methylenes), 2.23 (3H, s, CH$_3$), 3.75 (1H, m, C6-H), 4.41 (1H, m, C5-H), 6.02 (1H, br.d, J 16 Hz, CH$_3$COC$\underline{H}$=), 6.4-6.9 (2H, m, C3-H and —C$\underline{H}$=-CH—COCH$_3$), 7.40 and 7.46 (1H, 2×s, phthalidyl methine), and 7.5-7.95 (4H, m aromatic).

EXAMPLE 14

Pivaloyloxymethyl 6-(3-methoxycarbonyl-2-propen-1-yl)-7-oxo-1-azabicyclo[3,2,0]hept-2-ene-2-carboxylate

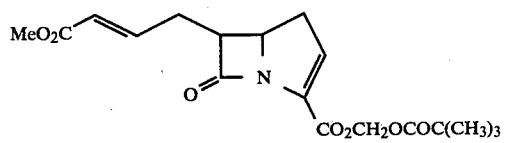

(i) 7-(1-Pivaloyloxymethyloxycarbonyl-1-triphenylphosphoranylidenemethyl)8-oxo-7-azabicyclo[4,2,0]oct-3-ene

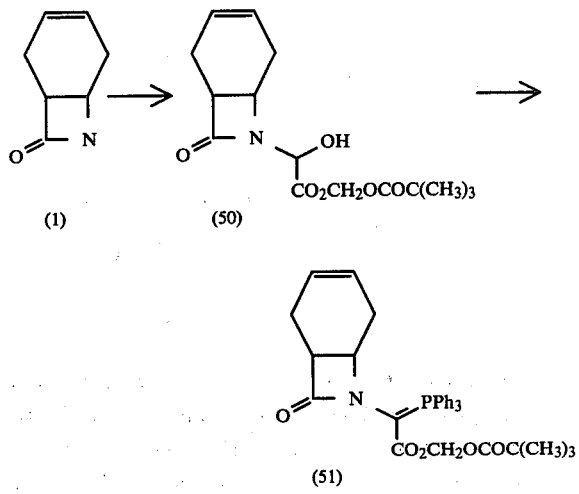

The azetidin-2-one (1) (0.4 g) in dimethylformamide (2 ml) was stirred with glyoxylic acid monohydrate (0.32 g) and 4 A type moleculaar sieves (4 chips) for 5 hours. Potassium carbonate (0.248 g) was added followed by pivaloyloxymethyl bromide (1.2 g). After stirring overnight the solution was diluted with ethyl acetate, washed with water, dried (MgSO4) and evaporated. The residual oil (0.8 g) was chromatographed on silica gel 60 (<230 mesh) eluting with ethyl acetate - petroleum ether (60°-80°) to give the alcohol (50), as a mixture of isomers, $\nu_{max}$ (CHCl3) 3460, 3300, 1755 (b) cm$^{-1}$.

This mixture (0.26 g) in tetraydrofuran (3 ml) was cooled to −20° and 2,6-lutidine (0.21 ml) followed by thionyl chloride (0.14 ml) were added with stirring. After 0.5 hours the reaction mixture was filtered, and the filtrate evaporated to dryness from toluene. The residue was dissolved in dioxan (2 ml). Triphenylphosphine (0.45 g) and 2,6-lutidine (0.21 ml) were added and the reaction stirred overnight at room temperature. The mixture was filtered, the filtrate evaporated and chromatograhed on silica gel 60 (≦230 mesh) to give the phosphorane (51) as a foam (0.291 g), $\nu_{max}$ (CHCl3) 1740, 1630 cm$^{-1}$.

(ii) Pivaloyloxymethyl 6-(3-methoxycarbonyl-2-propen-1-yl)-7-oxo-1-azabicyclo[3,2,0]hept-2-ene-2-carboxylate

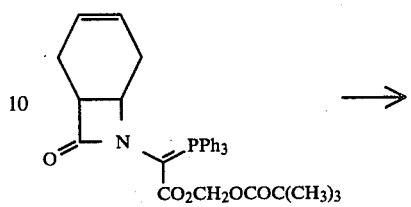

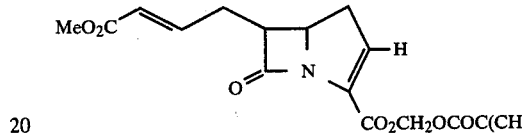

The phosophorane (51) (0.1 g) was dissolved in ethyl acetate (5 ml) and trifluoroacetic acid (1 ml) at room temperature. The solution was cooled (−70°) and treated with ozone until the reaction solution showed a slight blue colouration. Argon was blown through the solution to remove excess ozone and then triphenylphosphine (0.075 g) dissolved in ethyl acetate was added. After five minutes the reaction vessel was transferred to an ice-bath and saturated sodium hydrogen carbonate solution (30 ml) was added with vigorous stirring. The ethyl acetate layer was separated, dried (MgSO4), and kept for 45 minutes at room temperature. Methoxycarbonylmethylenetriphenylphosphorane (0.075 g) in the minimum volume of methylene chloride was added to the ethyl acetate solution. After one hour the solvent was removed and the residue chromatographed on silica gel 60 (<230 mesh) eluting with ethyl acetate-petroleum ether (60°-80°) to give the product (52) (25 mg), m.p. 110°-112° (from ether), $\lambda_{max}$ (EtOH) 210 and 275 nm (ϵ 4060), $\nu_{max}$(CHCl3) 1785, 1750, 1725, 1660, 1610 cm$^{-1}$. δ ppm (CDCl3) 1.22 (9H, s, Bu$^t$), 2.75 (2H, dd, J 9, 3 Hz, C4-H2), 2.40-2.90 (2H, m, CH2), 3.70 (3H, s, OMe), 3.65-3.90 (1H, m, C6-H), 4.40 (1H, dt, J 6, 9 Hz, C5-H), 5.81 (1H, dd, J$_t$ 15, 1 Hz, MeO2-C—CH═CHCH2), 5.81 and 5.84 (2H, inner signals ABq, CO2CH2O), 6.54 (1H, t, J 3 Hz, C3-H), 6.86 (1H, dt, J 6, 15 Hz, MeO2C—CH═CHCH2). (Found: C, 59.2; H, 6.4; N, 3.8%; M, 365.1498. C18H23NO7 requires C, 59.2; H, 6.3; N, 3.8%. M, 365.1475). The concentrations of this compound required to inhibit the growth of the following bacteria are given below:

| Organism | μg/ml (agar) |
|---|---|
| B. subtilis A | 20 |
| E. coli 0111 | 20 |
| Klebsiella aerogenes A | 20 |
| Salmonella typhimurium CT 10 | 20 |
| Shigella sonnei MB 11967 | 20 |
| Staph. aureus Oxford | 2 |
| Staph. aureus Russell | 2 |
| Staph. aureus 1517 | 2 |

EXAMPLE 15 p-Nitrobenzyl 6-(3-methoxycarbonyl-2-propen-1-yl)-7-oxo-1-azabicyclo[3,2,0]hept-2-ene-2-carboxylate

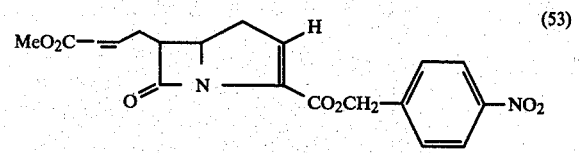
(53)

(i)

7-(1-Hydroxy-1-p-nitrobenzyloxycarbonylmethyl)-8-oxo-7-azabicyclo[4,2,0]-oct-3-ene

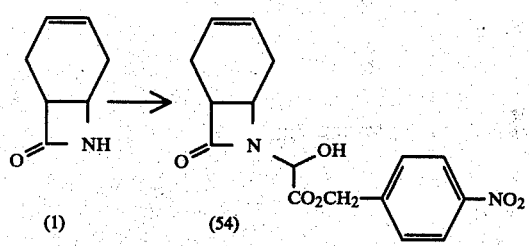

(1) (54)

p-Nitrobenzyl glyoxylate hydrate (9.08 g) was refluxed in benzene (150 ml) with provision for the removal of water. After 1 hour 8-oxo-7-azabicyclo[4.2.0]oct-3-ene (1) (2.46 g) was added and refluxing continued for 3.5 hours. The cooled solution was washed with water (x2), then brine. After back extraction of the first aqueous extract with ethyl acetate, the organic solutions were dried over magnesium sulphate, filtered combined, and evaporated. Chromatography on silica, eluting with ethyl acetate-petroleum ether mixtures gave two separate isomers of the alcohol (54) (43%). Less polar isomer I m.p. 153°–5° (crystalline plates ex ethyl acetate/ether). $\nu_{max}$ (CHCl$_3$) 3400 (broad), 1760, 1745, 1520, 1350 cm$^{-1}$. δ ppm (CDCl$_3$) 1.90-2.83 (4H, m, 2-CH$_2$), 3.23-3.55 (1H, m, β-lactam proton), 4.00-4.20 (1H,m, β-lactam proton), 4.27 (1H, d, J 8 Hz, exchangeable with D$_2$O, OH), 5.33 (2H, s, CH$_2$Ar)obscuring 1H, CHOH; 5.67-5.88 (2H, m, CH=CH), 7.55 (2H, d, J 8.5 Hz, Ar), 8.23 (2H, d, J 8.5 Hz, Ar) (Found: C, 58.07; H, 5.15; N, 8.51%. C$_{16}$H$_{16}$N$_2$O$_6$ requires C, 57.83; H, 4.85; N, 8.43%). More polar isomer II m.p. 118°–120° (fine crystalline needles ex ethyl acetate/ether). $\nu_{max}$ (CHCl$_3$) 3400 (broad), 1760-1745, 1520, 1350 cm$^{-1}$. δ ppm (CDCl$_3$) 1.83-2.77 (4H, m, 2-CH$_2$), 3.25-3.55 (1H, m, β-lactam proton), 4.02-4.37 (2H, m, β-lactam proton and CHOH, —OH exchangeable with D$_2$O), 5.31-5.98 [5H, 5.35 (2H, s, CH$_2$Ar), obscuring, 1H, which sharpens to s, at δ 5.40 and D$_2$O exchange, CHOH, and 2H, m, CH=CH], 7.56 (2H, d, J 8 Hz, Ar), 8.23 (2H, d, J 8 Hz, Ar) (Found: C, 57.95; H, 4.95; N, 8.50%. C$_{16}$H$_{16}$N$_2$O$_6$ requires C, 57.83; H, 4.85; N, 8.43%).

(ii)

7-(1-p-Nitrobenzyloxycarbonyl-1-triphenylphosphoranylidenemethyl)8-oxo-7-azabicyclo[4,2,0]oct-3-ene

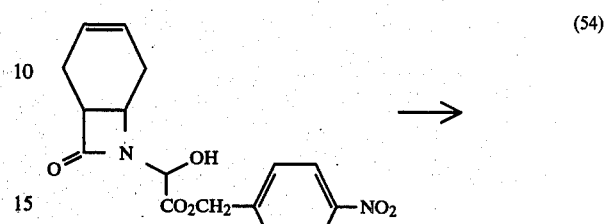
(54)

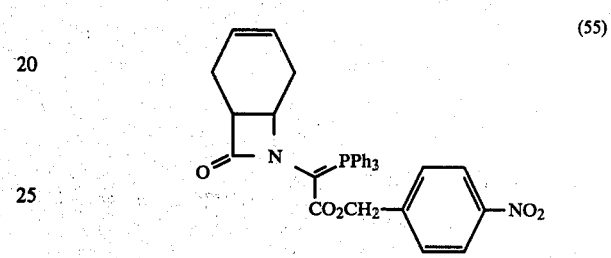
(55)

The alcohol (54), as a mixture of isomers, (1.86 g) in dry tetrahydrofuran (60 ml), under argon, was treated with lutidine (1.37 ml). To the solution, cooled to −20°, was added dropwise, with stirring, a solution of thionyl chloride (0.87 ml) in tetrahydrofuran (20 ml). A white solid came out of solution. The stirred mixture was allowed to reach room temperature over 20 minutes and was filtered and evaporated to dryness. The residue in dry dioxan (60 ml) was treated with triphenylphosphine (3.12 g) and lutidine (1.37 ml) and left stirring overnight at room temperature. The lutidine hydrochloride was separated by filtration, and the filtrate evaporated. The residue was taken up in ethyl acetate, washed with, water containing a few drops of hydrochloric acid, water then brine, dried over magnesium sulphate, filtered and evaporated. Chromatography on silica, eluting with ethyl acetate/petroleum ether mixtures gave the phosphorane (55, 2.68 g) as an amorphous solid. $\nu_{max}$ (CHCl$_3$) 1738, 1620 (shoulder), 1605, 1520, 1350 cm$^{-1}$.

(iii) p-Nitrobenzyl 6-(3-methoxycarbonyl-2-propen-1-yl)-7-oxo-1-azabicyclo[3,2,0]hept-2-ene-2-carboxylate

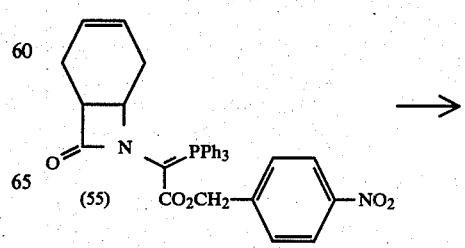
(55)

-continued

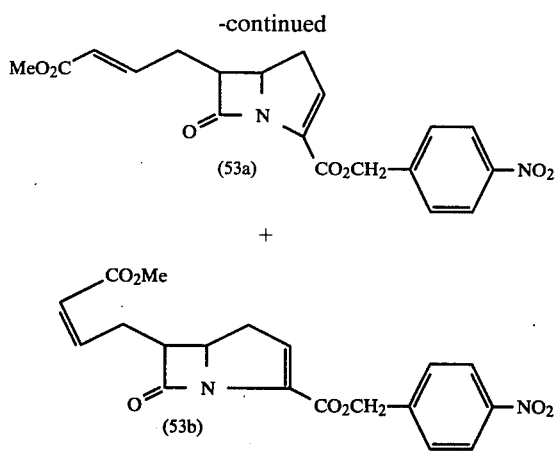

The phosphorane (55) (0.4 g) in ethyl acetate (30 ml) was treated with trifluoroacetic acid (1.61 ml). The solution was cooled (−70°) and treated with ozone until pale blue. Argon was blown through the solution to remove excess ozone, and then triphenylphosphine (0.272 mg) dissolved in ethyl acetate (5 ml) was added. After five minutes the reaction was transferred to an ice-bath and stirred vigorously with saturated aqueous sodium bicarbonate (30 ml), for 10 minutes. The organic phase was separated, dried over magnesium sulphate and filtered. The pale solution was stood at room temperature for 1.25 hours, then reduced to 15 ml by evaporation, and treated with carbomethoxymethylene triphenylphosphorane (0.26 g). After 30 minutes the solution was evaporated. Rapid chromatography of the residue on 4 g silica, eluting with ethyl acetate/petroleum ether mixtures gave the trans (about the C6-double bond) isomer (53a) (132 mg) m.p. 156°-9° (ex. ethyl acetate/petroleum ether), $\lambda_{max}$ (ethanol) 269 nm ($\epsilon$ 14,300); $\nu_{max}$ (CHCl$_3$) 1782, 1722, 1655 (weak), 1605 (weak), 1525, 1350 cm$^{-1}$. δ ppm (CDCl$_3$) 2.73 (2H, dd, J 9.5, 3 Hz, C4-H), - partially obscuring 2.25-2.90 (2H, m, side-chain CH$_2$), 3.69 (3H, s, CH$_3$), - partially obscuring 3.74 (1H, td, J 9.5, 6 Hz, C5-H) 4.39 (1H, td, J 9.5, 6 Hz, C6-H), 5.20 and 5.42 (2H, ABq, J 14 Hz, CH$_2$Ar), 5.80 (1H, d, J 16 Hz, trans CH=CHCH$_2$), 6.53 (1H, t, J 3 Hz, C3-H), 6.85 (1H, td, J 6, 16 Hz, trans CH=CHCH$_2$), 7.52 (2H, d, J 8 Hz, Ar), 8.14 (2H, d, J 8 Hz, Ar); (Found: C, 58.90; H, 4.70; N, 7.08. C$_{19}$H$_{18}$N$_2$O$_7$ requires C, 59.06; H, 4.70; N, 7.25%).

The concentrations of this compound required to inhibit the growth of the following bacteria are given below.

| Organism | μg/ml (agar) |
|---|---|
| *Staph. aureus* Russell | 2.46 |
| *Strep. pneumoniae* | 7.4 |
| *Strep. pyogenes* | 0.8 |

A small amount (4 mg) of the cis isomer (53b) was also obtained m.p. 109°-111° (ex ether) $\lambda_{max}$ (ethanol 269 nm ($\epsilon$ 13,950), $\nu_{max}$ (CHCl$_3$) 1778, 1720, 1650 (weak), 1520, 1350 cm$^{-1}$. δ ppm (CDCl$_3$) 2.40-3.50 (4H, m, 2-CH$_2$), 3.66 (3H, s, CH$_3$), partially obscuring, 3.73 (1H, td, J 8 Hz, 6 Hz, C6-H), 4.35 (1H, td, J 9.5, 6 Hz, C5-H), 5.19 and 5.40 (2H, ABq, J 14 Hz, CH$_2$Ar), 5.84 (1H, d, J 11 Hz, cis CH=CHCH$_2$), 6.22 (1H, ddd, J 11, 8 6 Hz, cis CH=CHCH$_2$), 6.55 (1H, t, J 3 Hz, C3-H), 7.52 (2H, d, J 8 Hz, Ar), 8.14 (2H d, J 8 Hz, Ar).

EXAMPLE 16

Benzyl 6-(3-cyano-2-propen-1-yl)-7-oxo-1-azabicyclo[3,2,0-]hept-2-ene-2-carboxylate

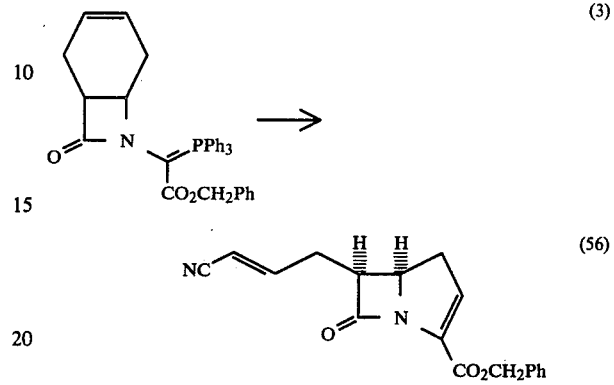

The phosphorane (3) (1 g) was dissolved in ethyl acetate (50 ml) and treated with trifluoroacetic acid (1.25 ml). After five minutes at room temperature the reaction mixture was cooled to −70°. Ozone was blown into the solution until it was pale blue. The excess ozone was then removed with a stream of argon. Triphenylphosphine (0.5 g) in ethyl acetate was added. After five minutes the mixture was transferred to an ice-bath and saturated sodium hydrogen carbonate solution (40 ml) was added with vigorous agitation. The organic phase was separated dried (MgSO$_4$) and treated with cyanomethylenetriphenylphosphorane (0.55 g) with stirring. After 40 minutes at room temperature the solution was evaporated to dryness and chromatographed on silica gel 60 (<230 mesh) eluting with 3:7 ethyl acetate: 60°-80° petroleum ether to give (56)(0.054 g of pure product obtained followed by 0.183 g contaminated with some triphenylphosphine oxide) showing $\nu_{max}$ (CHCl$_3$) 2250 (CN), 1785, 1730, 1640, 1620 cm$^{-1}$. δ ppm (CDCl$_3$) 2.45-2.90 (2H, m, CH$_2$), 2.73 (2H, dd, J 9, 3 Hz, C4-H$_2$), 3.60-3.90 (1H, m, C6-H), 4.40 (1H, dt, J 9, 6 Hz, C5-H), 5.25 (2H, s, CH$_2$), 5.40 (1H, dd, J 16, 1 Hz), 6.53 (1H, t, J 3 Hz), 6.60 (1H, dt, J 16, 7 Hz), 7.30 (5H, s, Ar). (Found: M, 308.1120. C$_{18}$H$_{16}$N$_2$O$_3$ requires M, 308.1161).

The concentrations of this compound required to inhibit the growth of the following bacteria are given below.

| Organism | μg/ml (agar) |
|---|---|
| *B. subtilis* A | 20 |
| *Citrobacter freundii* E8 | 20 |
| *Enterobacter cloacae* N1 | 20 |
| *E. coli* 0111 | 20 |
| *Klebsiella aerogenes* A | 20 |
| *Proteus mirabilis* C977 | 20 |
| *Proteus morganii* I 580 | 20 |
| *Proteus rettgeri* WM16 | 20 |
| *Salmonella typhimurium* CT10 | 20 |
| *Serratia marcescens* US20 | 20 |
| *Shigella sonnei* MB 11967 | 20 |
| *Staph. aureus* Oxford | ≦2 |
| *Staph. aureus* Russell | ≦2 |
| *Staph. aureus* 1517 | ≦2 |

EXAMPLE 17

Benzyl 6-(4-Oxo-2-penten-1-yl)-7-oxo-1-azabicyclo[3,2,0]hept-2-ene-2-carboxylate

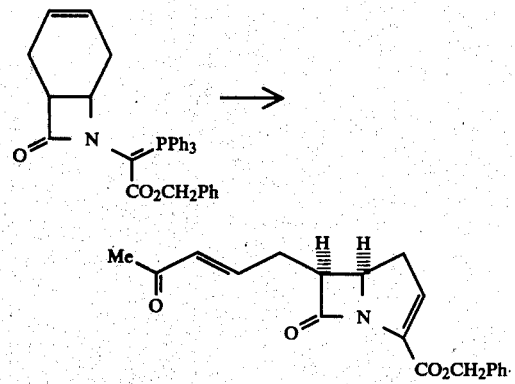

The phosphorane (3) (1 g) was dissolved in ethyl acetate (50 ml) and trifluoroacetic (1.25 ml). After cooling to −70° ozone was bubbled into the solution until it was pale blue. Excess ozone was then removed with a stream of argon and triphenylphosphine (0.5 g) in ethyl acetate (10 ml) was added. After five minutes the solution was transferred to an ice bath and neutralized with saturated sodium bicarbonate solution (40 ml) with vigorous agitation. The organic phase was separated, dried (MgSO$_4$) filtered and the solution made up to 100 ml with ethyl acetate. The aliquot of this solution (50 ml) containing the aldehyde (4) was treated with acetylmethylenetriphenylphosphorane (0.293 g) with stirring. The reaction solution was left at room temperature overnight (18 h). The ethyl acetate was evaporated under reduced pressure and the residue rapidly chromatographed on silica gel 60 (15 g) (<230 mesh) eluting initially with 3:7 ethyl acetate: 60°–80° petroleum ether and then 1:1 ethyl acetate:petroleum ether. The product (57) was contaminated with triphenylphosphine oxide and therefore rechromatographed to give pure (57) (0.05 g) as a gum, $\nu_{max}$ (CHCl$_3$) 1785, 1730, 1680, 1630, 1620 cm$^{-1}$. $\delta$ ppm (CDCl$_3$) 2.25 (3H, s, COCH$_3$), 2.50–3.00 (4H, m, 2×CH$_2$), 3.55–3.95 (1H, m, C6-H), 4.40 (1H, dt, J 9 m 6 Hzm C5-H), 5.25 (2H, s), 6.15 (1H, d, J 16 Hz), 6.50 (1H, t, J 3 Hz, C3-H), 6.75 (1H, dt, J 16, 7 Hz), 7.30 (5H, s, Ar). (Found: M, 325.1345. C$_{19}$H$_{19}$NO$_4$ requires M, 325.1376).

EXAMPLE 18 p-Bromophenacyl 6-(3-methoxycarbonyl-2-propen-1-yl)-7-oxo-1-azabicyclo[3.2.0]hept-2-ene-2-carboxylate

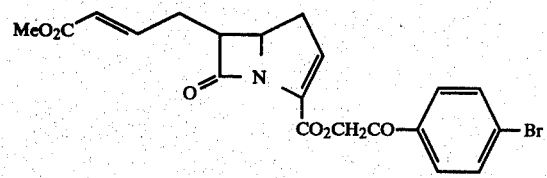

(i) 7-(1-Hydroxy-1-p-bromophenacyloxycarbonylmethyl)-8-oxo-7-azabicyclo[4.2.0]oct-3-ene

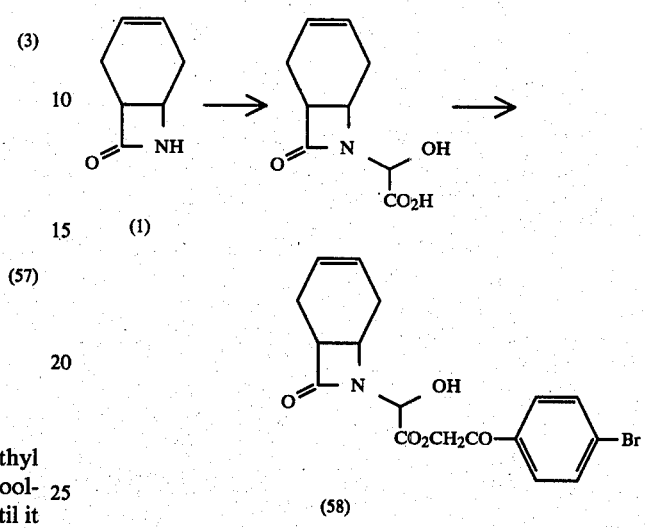

The azetidinone (1) (0.4 g) in anhydrous dimethylformamide (2 ml) was stirred with glyoxylic acid hydrate (0.32 g) in the presence of hexamethylphosphorictriamide (0.1 ml) and molecular sieves (3 A; 4 pieces) for 5 h. Potassium carbonate (0.226 g) was added, and the solution stirred until effervescence had ceased (5 min.). p-Bromophenacylbromide (1.00 g; 1.05 equiv.) in dimethylformamide (1.0 ml) and hexamethylphosphorictriamide (0.25 ml) was added, and the solution stirred overnight. The solution was diluted with ethyl acetate, washed with saturated aqueous sodium chloride solution (x 3), dried (Na$_2$SO$_4$) and evaporated to give a gum (1.9 g) which was chromatographed on Kieselgel. Elution of the column with ethyl acetate-petroleum ether (1:1) gave the glyoxylate ester (58). Isomer I as a foam, which slowly crystallised (ethyl acetate-petroleum ether) as needles (0.60 g.) (47%) m.p. 135°–136°, $\nu_{max}$ (CHCl$_3$) 3250br, 1760sh, 1750, 1710, 1590, 970 cm$^{-1}$; $\delta$(d$_6$DMSO) 1.9–2.8 (4H, m), 3.35 (1H, m), 4.17 (1H, m) 5.51 (1H, d, J 6.5 Hz; sharpens to a signlet on D$_2$O exchange) 5.55 (2H, s, phenacyl CH$_2$), 5.72br (2H, s), 6.81 (1H, d, J 6.5H, D$_2$O enchangeable), 7.75 (2H, d, J 9 Hz) and 7.90 (2H, d, J 9 Hz) (Found: C, 51.9; H, 4.2; N, 3.6; Br, 20.00. C$_{17}$H$_{16}$BrNO$_5$ requires C, 51.8; H, 4.1; N, 3.6; Br, 20.3%).

Continued elution of the column gave the more polar Isomer II, which crystallised (ethyl acetate-petroleum ether) as platelets (0.55 g) (43%), m.p. 144°–146°, $\nu_{max}$ (CHCl$_3$) 3200br, 1760sh, 1750, 1710, 1590, 965 cm$^{-1}$; $\delta$ (d$_6$DMSO) 1.9–2.8 (4H, m), 3.33 (1H, m) 4.15 (1H, m), 5.47 (1H, d, sharpens to a singlet on D$_2$O exchange), 5.51 (2H, s, phenacyl CH$_2$), 5.71br (2H, s), 6.90 (1H, d, J 7 Hz, D$_2$O exchangeable), 7.73 (2H, d, J 9 Hz), and 7.91 (2H, d, J 9 Hz). (Found: C, 51.7; H, 4.3; N, 3.3; Br, 20.6.

(ii)

7-(1-p-bromophenacyloxycarbonyl-1-triphenylphor-phoranylidenemethyl)-8-oxo-7-azabicyclo[4.2.0]oct-3-ene

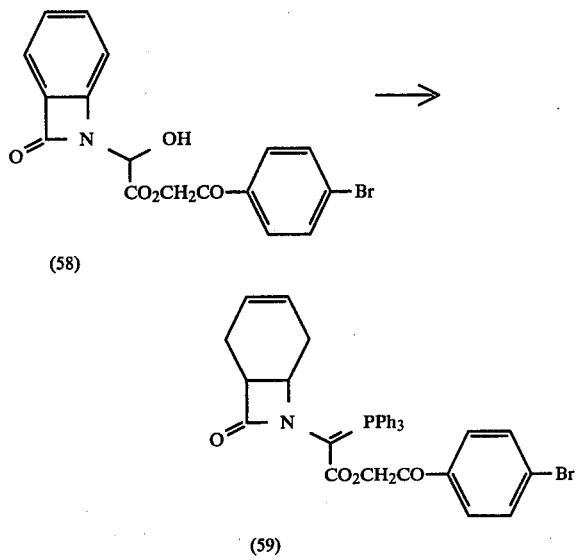

The glyoxylate p-bromophenacyl ester (58) (0.383 g; 1:1 isomer ratio) in THF (8 ml) was treated with lutidine (230 μl), followed by thionyl chloride (139 μl) at −20° for 3.5 h. The material was, rapidly filtered through celite, washed with ethyl acetate, and the filtrate and washings evaporated in vacuo. The residue in dioxan (4 ml, anhydrous) was treated with triphenylphosphine (0.51 g) and lutidine (230 μl) at room temperature overnight. Chromatography on Kieselgel (elution with ethyl acetate petroleum ether, 7:3) gave the phosphorane (59) as a gum (0.536 g) which crystallised from ethyl acetate-ether-petroleum ether as small rods (0.499 g.) (80%) m.p. 200°–202°, $\nu_{max}$ (CHCl$_3$) 1740st, 1710, 1620, 1590, 1480 cm$^{-1}$. (Found: C, 65.7; H, 4.7; N, 2.0; Br, 12.1. C$_{35}$H$_{29}$BrNO$_4$P requires C, 65.8; H, 4.6; N, 2.2; Br, 12.5%).

(iii)

p-Bromophenacyl-6(3-methoxycarbonyl-2-propen-1-yl)-7-oxo-1-azabicyclo[3.2.0]hept-2-ene-2-carboxylate

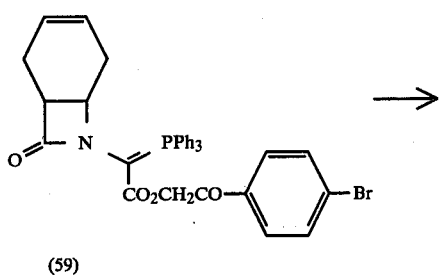

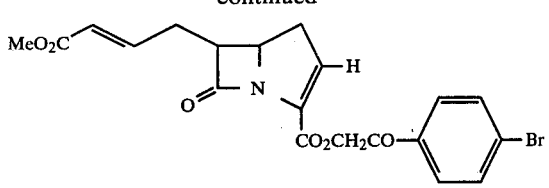

The phosphorane (59) (0.104 g) was converted to the bicyclic ester (60) and isolated by the method described for the benzyl ester in example 2. The product (60) (35 mg) crystallised from ethyl acetate-petroleum ester and had m.p. 134°–136°, $\nu_{max}$ 1785, 1725sh, 1715, 1700, 1660, 1610, 1590 cm$^{-1}$; $\lambda_{max}$ (EtOH) infl 275, 258 ($\epsilon$21900), 210 (26,000); $\delta$(CDCl$_3$) 2.45–2.9 (2H, m, C6 side-chain CH$_2$), 2.74 (2H, dd, J 9, 3 Hz, C4-H$_2$), 3.68 (3H, s), 3.6–3.9 (1H, m, C$_6$-H), 4.40 (1H, dt, J 9, 6 Hz, C5-H), 5.36 (2H, s), 5.80 (1H, dt, J 15, 1 Hz), 6.60 (1H, t, J 3 Hz, C3-H), 6.86 (1H, dt, J 15, 6 Hz), 7.55 (2H, d, J 9 Hz) and 7.74 (2H, d, J 9 Hz). (Found: C, 53.4; H, 4.1; N, 3.2; Br, 17.9. C$_{20}$H$_{18}$BrNO$_6$ requires C, 53.6; H, 4.0; N, 3.1; Br, 17.8%).

EXAMPLE 19

Pnthalidyl 6-(3-cyano-2-propen-1-yl)-7-oxo-1-azabicyclo[3.2.0-]hept-2-ene-2-carboxylate

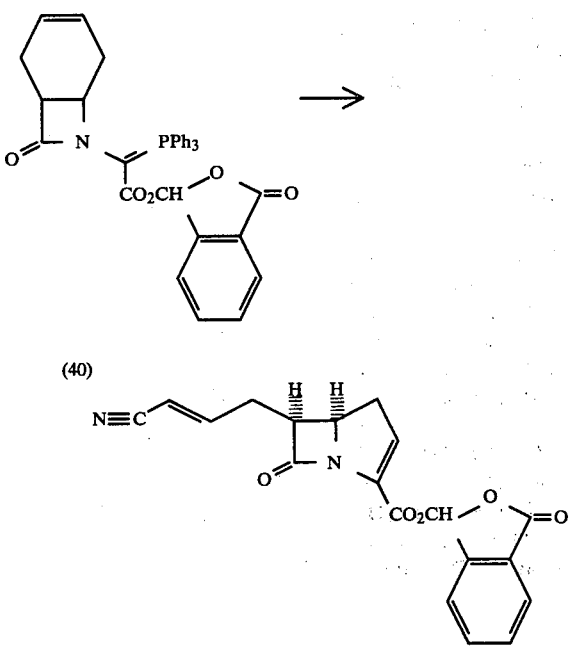

The phosphorane (40) (0.345 g) was dissolved in 5:1 ethyl acetate/trifluoroacetic acid (15 ml) and the solution left at room temperature for 15 minutes. The solution was then cooled (−70°) and ozone passed through the solution until it became slight blue. Argon was passed through the solution to remove excess ozone and triphenylphosphine (0.2 g) in ethyl acetate (10 ml) was added. The mixture was transferred to an ice-bath, diluted with ethyl acetate (50 ml), and then saturated sodium bicarbonate solution (75 ml) was added with vigorous agitation. The organic phase was separated and the aqueous layer extracted again with ethyl acetate (30 ml). The combined organic layers were dried (Na₂SO₄), filtered and left to stand at room temperature for 4½ hours over 4A molecular sieves.

Cyanomethylenetriphenylphosphorane (0.18 g) was dissolved in ethyl acetate (30 ml). The reaction solution was filtered to remove the sieves and then treated with the solution of phosphorane. The reaction solution was reduced in volume (in vacuo) to about 30 ml and left at room temperature for 1 hour. The solution was evaporated to dryness and chromatographed rapidly through a column (5 g) of silica gel (<230 mesh) eluting with 1:1 ethyl acetate: 60°–80° petroleum ether. The product (62 mg) (containing some Ph₃P=O) was triturated with 1:1 ethyl acetate:petroleum-ether 60°–80° to give the ester (61) (12 mg), as a white solid, $\nu_{max}$ (CHCl₃) 2225 (C≡N), 1790 (β-lactam and lactone), 1745 (ester), 1640 (side chain double bond), 1615 (ring double bond) cm⁻¹.

The concentrations of this compound required to inhibit the growth of the following bacteria are given below:

| Organism | μg/ml (agar) |
|---|---|
| *Citrobacter fruendii* E8 | 7.3 |
| *Enterobacter cloacae* N1 | 22 |
| *E. coli* O111 | 7.3 |
| *Klebsiella aerogenes* | 7.3 |
| *Proteus mirabilis* C977 | 66.6 |
| *Proteus morganii* I 580 | 22 |
| *Proteus rettgeri* WM 16 | 22 |
| *Proteus vulgaris* WO 91 | 66.6 |
| *Salmonella typhimurium* | 7 |
| *Serratia marcescens* US20 | 22 |
| *Shigella sonnei* MB 11967 | 22 |
| *Staph. aureus* Oxford | 2.4 |
| *Staph. aureus* Russell | 2.4 |

EXAMPLE 20

Benzyl 7-oxo-1-azabicyclo[3.2.0]hept-2-ene-2-carboxylate

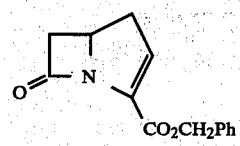

(i) Preparation of benzyl 7-oxo-1-azabicyclo[3.2.0]hept-2-ene-2-carboxylate

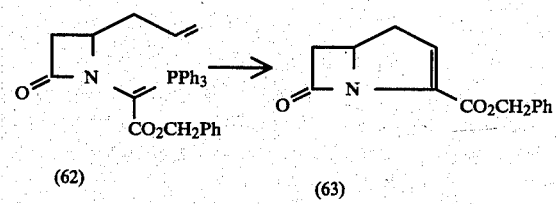

The phosphorane (62) (500 mg) in ethyl acetate (60 ml) was treated with trifluoroacetic acid (0.7 ml). After cooling to −70° ozone was passed into the solution until it became pale blue. Argon was then passed through to remove excess ozone and then triphenylphosphine (250 mg) in ethyl acetate (5 ml) was added. After stirring for 5 minutes the reaction flask was transferred to an ice-bath and saturated aqueous sodium bicarbonate (50 ml) was added. After stirring vigorously for 40 minutes the mixture was diluted with more ethyl acetate, and the organic phase washed with brine, dried over magnesium sulphate and evaporated to a gum. Chromatography on silica gel, eluting with ethyl acetate-petroleum ether mixtures gave the bicyclic compound (63) as an oil (110 mg). $\nu_{max}$ (CHCl₃), 1782, 1725 cm⁻¹. δ ppm (CDCl₃) 2.68 (1H, ddd, J 16 Hz, 9 Hz, 3 Hz, C4-H); 2.90 (1H, ddd, J 16 Hz, 9 Hz, 3 Hz, C4-H), [2.92 (1H, dd, J 16 Hz, 3.5 Hz) and 3.45 (1H, dd, J 16 Hz, 5.5 Hz), collapsing to ABq J 16 Hz on irradiation at δ4.23, C6-CH₂], 4.24 (1H, m. collapsing to d, J 5.5 Hz on irradiation at δ2.80, C5-H), 5.20 (2H, s, CH₂Ph), 6.44 (1H, t, J 3 Hz, collapsing to s on irradiation at δ2.80 (C3-H), 7.30 (5H, s, Ph) (Found: M, 243.0883 C₁₄H₁₃NO₃ requires M, 243.0895).

EXAMPLE 21 t-Butyl 7-oxo-1-azabicyclo[3,2,0]hept-2-ene-2-carboxylate

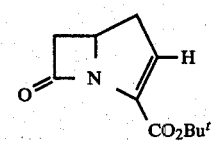

(i) Preparation of 4-allyl-1-(1-hydroxy-1-tert-butyloxycarbonylmethyl)azetidin-2-one

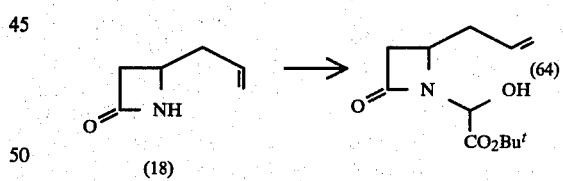

tert-Butyl glyoxylate hydrate (6.22 g) in benzene (120 ml) was refluxed for 1 hour in a Dean-Stark apparatus to remove the water. The azetidinone (18) (2.31 g) was then added and the reaction mixture refluxed for 4 hours. Chromatography of the crude product as in Example 4(iv) gave the alcohol (64) as a pale yellow oil (4.48 g). $\nu_{max}$ (CHCH₃) 3490, 1755, 1735, 1640 (weak) cm⁻¹ δppm (CDCl₃) 1.50 (9H, s, Buᵗ), 2.20–3.25 [4H, 2.66 (1H, dd, J 3 Hz, 14 Hz, C3-H), and 3.09 (1H, dd, J 14 Hz, 5 Hz, C3-H) obscurring 2H, CH₂]; 3.68–4.10 (1H, m, C4-H), 4.47 (1H, broad s, exch. D₂O, OH); 4.98–5.37 (3H, m, sharpening with D₂O), 5.52–6.23 (1H, m, CH=CH₂). M⁺ at m/e 241 and (m/e+1).

(ii) Preparation of 4-allyl-1-(1-tert-butyloxycarbonyl-1-triphenylphosporanylidene methyl)azetidine-2-one

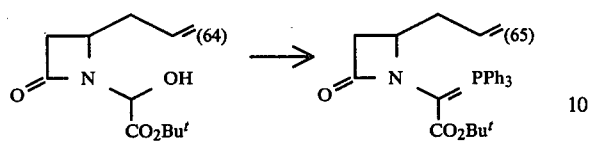

A stirred solution of the alcohol (64) (4.2 g) in dry tetrahydrofuran (120 ml) under argon, was cooled to −20°, and treated with lutidine (4.03 ml) in tetrahydrofuran (15 ml). Thionyl chloride (2.54 ml) in tetrahydrofuran (15 ml) was added dropwise. After allowing to reach 0° over 30 minutes, the solution was filtered, the lutidine hydrochloride being washed with toluene.

The combined filtrate and washings were evaporated to dryness. the residue was taken up in dry dioxan (100 ml) and treated with lutidine (4.03 ml) and triphenylphosphine (9.1 g). After stirring at room temperature overnight, the phosphorane (65) was isolated as in Example 4 (v) and obtained as white crystals (4.62 g) from ether mp. 188°-9°, $\nu_{max}$ (CHCl$_3$) 1730, 1638, 1610 cm$^{-1}$ (Found: C, 74.1; H, 6.8; N, 3.0, P, 6.2% C$_{30}$H$_{32}$NO$_3$P requires C, 74.2, H, 6.6, N, 2.9, P, 6.4%).

(iii) Preparation of tert-Butyl 7-oxo-1-azabicyclo[3.2.0]hept-2-ene-2-carboxylate

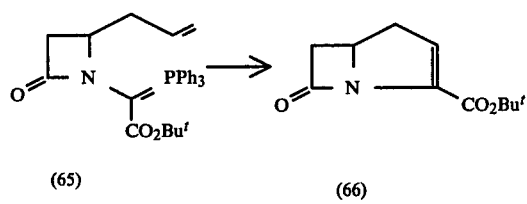

The phosphorane (65) (242 mg) in ethyl acetate (15 ml) was treated with trifluoroacetic acid (0.38 ml). After cooling to −70°, ozone was passed into the solution until it became pale blue. After passing argon through to remove excess ozone, triphenylphosphine (131 mg) in ethyl acetate (1 ml) was added. After stirring for 5 minutes the reaction flask was transferred to an ice-bath and saturated aqueous sodium bicarbonate (20 ml) was added. The mixture was stirred vigorously for 30 minutes and the organic phase separated and washed with water. The aqueous phase was re-extracted with ethyl acetate. The combined organic extracts were dried over magnesium sulphate, evaporated and the residue chromatographed on silica gel eluting with ethyl acetate-petroleum ether mixtures, to give the bicyclic compound (66) as an oil (50 mg) $\nu_{max}$ (CHCl$_3$) 1780, 1710, 1610 cm$^{-1}$. δppm (CDCl$_3$) 1.49 (9H, s, Bu$^t$), 2.70 (1H, ddd, J 19 Hz, 10 Hz, 2 Hz, C4-H), 2.87 (1H, ddd, J 19 Hz, 9 Hz, 2 Hz, C4-H), 2.86 (1H, dd, J 14 Hz, 2.5 Hz, C6-H), 3.40 (1H, dd, J 14 Hz, 5 Hz, C6-H), 3.99-4.33 (1H, m, C5-H), 4.26 (1H, t, J 2 Hz, C3-H). (Found: M, 209.1050 C$_{11}$H$_{15}$NO$_3$ requires M, 209.1052).

EXAMPLE 22 t-Butyl 3-methyl-7-oxo-1-azabicyclo[3.2.0]hept-2-ene-2-carboxylate

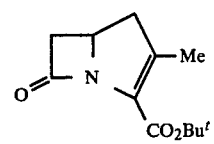

(i) Preparation of 4-(propan-2-one)azetidin-2-one

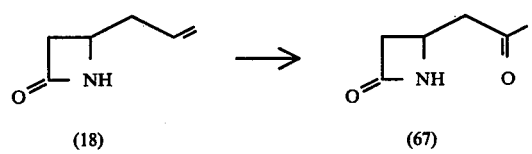

4-Allyl-azetidin-2-one (18) (0.22 g, 2 mmoles) and mercuric acetate (0.64 g, 2 mmoles) were stirred at room temperature for 2 hours in methanol (6 ml). This solution was added to a mixture of cupric chloride dihydrate (1.03 g, 6 mmoles) and palladous chloride (0.034 g, 0.2 mmoles) in methanol (6 ml). After heating for 1 hour at 60° C., the reaction mixture was cooled and saturated aqueous sodium hydrogen carbonate was added until the solution was at pH 9. The reaction mixture was filtered and the methanol removed under reduced pressure. Extraction of the aqueous phase with ethyl acetate (3×25 ml) followed by drying (MgSO$_4$) and removal of solvent, gave a green oil. Chromatography (silica eluted with pet. ether-ethyl acetate-ethanol) gave the ketone (67) (0.17 g, 70%) as an oil, $\nu_{max}$ (CHCl$_3$) 3420, 3000, 1760, and 1720 cm$^{-1}$; δ(CDCl$_3$) 2.14 (3H, s, CH$_3$), 2.4–3.4 (4H, m, methylenes), 3.86 (1H, m, C4-H), and 6.75 (1H, br, NH), (Found: M, 127.0628. C$_6$H$_9$NO$_2$ requires M, 127.0634).

(ii) Preparation of 1-(1-Hydroxy-1-t-butoxycarbonylmethyl)-4-(propan-2-one)azetidin-2-one

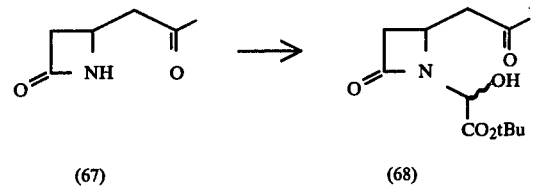

t-Butyl glyoxylate hydrate (0.3 g, 2.33 mmoles) was heated under reflux in benzene (10 ml) for 1 hour in an apparatus with provision for water removal. The ketone (67) (0.14 g, 1.1 mmoles) in dry benzene (3 ml) was added and the mixture was heated under reflux for 4 hours. Removal of solvent under reduced pressure followed by chromatography (silica eluted with pet. ether-ethyl acetate) gave the keto-alcohol (68) (0.196 g, 82%), δ(CDCl$_3$) 1.55 (9H, s, t-Bu), 2.23 (3H, s, CH$_3$), 2.5–3.5 (4H, m, methylenes), 4.20 (1H, m, C4-H), and 4.6–5.5 (2H, m, CHOH); and unchanged ketone (0.022 g).

(iii) Preparation of 1-(1-t-butoxycarbonyl-1-triphenylphosphoranylidenemethyl)-4-(propan-2-one)azetidin-2-one

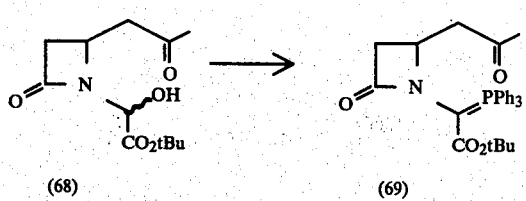

To a stirred solution of the keto-alcohol (68) (0.196 g, 0.763 mmoles) in dry tetrahydrofuran (5 ml) at −20° C. was added in turn 2,6-lutidine (0.163 g, 0.177 ml, 1.52 mmoles) and thionylchloride (0.181 g, 0.11 ml, 1.52 mmoles) in tetrahydrofuran (1 ml). The stirring was continued at −20° C. for 20 minutes. The solution was filtered, and the solvent was removed under reduced pressure and the residue was dried by azeotroping twice with toluene (10 ml). The resulting slurry was dissolved in dioxan (7 ml) and 2,6-lutidine (0.163 g, 0.177 ml, 1.52 mmoles) and triphenylphosphine (0.4 g, 1.52 mmoles) were added in turn. After stirring for 16 hours, the solution was filtered and the solvent was removed under reduced pressure. Chromatography (silica eluted with pet. ether-ethyl acetate) gave a semi-crystalline oil which couldbe crystallized by the addition of ether to give the phosphorane (69) (0.255 g, 70%) as white needles m.p. 176.5°–177.5°, $\nu_{max}$ (CHCl$_3$) 2990, 1740, 1720, and 1640 cm$^{-1}$, $\delta$(CDCl$_3$) 0.9 (9H, s, t-Bu), 1.4 (3H, s, CH$_3$), 2.18 (4H, m, methylenes), 3.14 (1H, m, C4-H), and 7.1–7.9 (15H, m, Ph). (Found: C, 71.8; H, 6.4; N, 2.7% C$_{30}$H$_{32}$NO$_4$P requires C, 71.8; H, 6.4; N, 2.8%)

(iv) Preparation of t-Butyl 3-methyl-7-oxo-1-azabicyclo[3,2,0]hept-2-ene-2-carboxylate

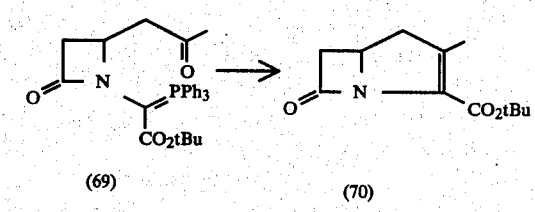

The phosphorane (69) (0.062 g, 0.124 mmoles) was heated in dry toluene (5 ml) under argon for 1½ hours at 100° C. The toluene was removed under reduced pressure and the residue chromatographed (silica eluted with pet. ether-ethyl acetate) to give the bicyclic product (70) (0.023 g, 83%) as an oil having $\nu_{max}$ (CHCl$_3$) 2970, 1775, 1700, and 1635 cm$^{-1}$, $\lambda_{max}$ (EtOH) 272 nm ($\epsilon$4000). $\delta$(CDCl$_3$) 1.51 (9H, s, tBu), 2.04 (3H, t, J 1.5 Hz, CH$_3$), 2.73 (2H, br d, J 9 Hz, C4-H), 2.77 (1H, dd, J 3, 16 Hz, C6-H), 3.35 (1H, dd, J 6, 16 Hz, C6-H), and 4.05 (1H, m, C5-H). (Found: M, 223.1212. C$_{12}$H$_{17}$NO$_3$ requires M, 223.1208).

EXAMPLE 23 p-Nitrobenzyl 3-methyl-7-oxo-1-azabicyclo[3,2,0]hept-2-ene-2-carboxylate

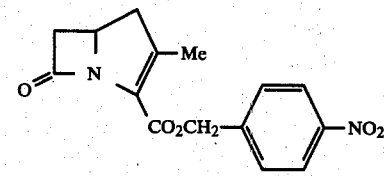

(i) Preparation of 1-(1-Hydroxy-1-p-nitrobenzyloxycarbonylmethyl)-4-(propan-2-one)azetidin-2-one

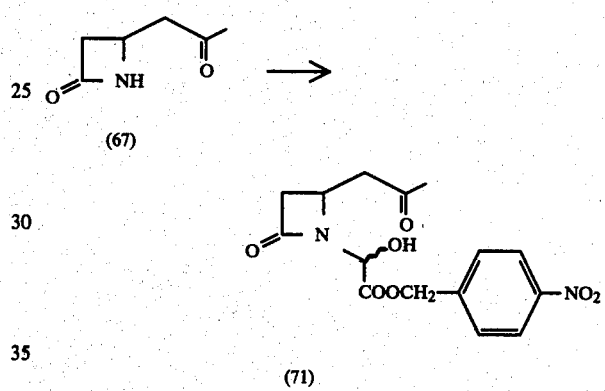

p-Nitrobenzyl glyoxylate hydrate (2.64 g, 11.6 mmoles) was heated under reflux in benzene (50 ml) for 1 hour in an apparatus with provision for water removal. The ketone (67) (0.8 g, 5.5 mmoles) in dry benzene (10 ml) was added and the mixture was heated under reflux for 7 hours. Removal of solvent under reduced pressure followed by chromatography (silica eluted with pet. ether-ethyl acetate) gave the keto-alcohol (71) (1.39 g, 75%) as a colourless oil, $\nu_{max}$ (CHCl$_3$) 3450, 1760, 1715, 1605, 1520 and 1345 cm$^{-1}$, $\delta$(CDCl$_3$) 2.17 (3H, d, CH$_3$), 2.46–3.54 (4H, m, $\beta$-lactam and $\alpha$-ketomethylenes), 4.20 (1H, m, C4-H), 4.50–5.8 (2H, m, CHOH), 5.40 (2H, d, benzylmethylene) and 7.50–8.40 (4H, m, aromatic).

(ii) Preparation of 1-(1-p-Nitrobenzyloxycarbonyl-1-triphenylphosphoranylidenemethyl)-4-(propan-2-one)azetidin-2-one

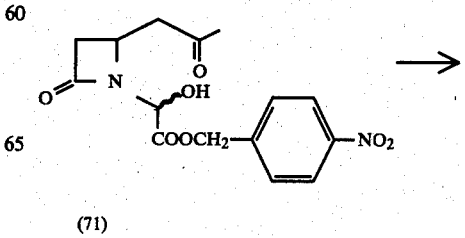

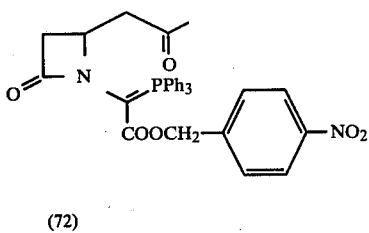

(72)

To a stirred solution of the keto-alcohol (71) (0.611 g. 1.84 mmoles) in dry tetrahydrofuran (13 ml) at −20° C. was added in turn 2,6-lutidine (0.39 g, 0.424 ml, 3.68 mmoles) and thionyl chloride (0.433 g, 0.264 ml, 3.68 mmoles) in tetrahydrofuran (2 ml). The stirring was continued at −20° C. for 20 minutes. The solution was filtered, and the solvent was removed under reduced pressure and the residue was dried by azeotroping twice with toluene (20 ml). The resulting slurry was dissolved in dioxan (15 ml) and 2,6-lutidine (0.39 g, 0.424 ml, 3.68 mmoles) and triphenylphosphine (0.95 g, 3.68 mmoles) were added in turn. After stirring for 2 hours, the solution was filtered and the solvent was removed under reduced pressure. Chromatography (silica eluted with pet. ether-ethyl acetate-dioxan) gave the phosphorane (72) (0.73 g, 70%) as a yellow crystals m.p. 185°–187°, $\nu_{max}$ (CHCl$_3$) 2990, 1740, 1715, 1630, 1610, 1520, and 1350 cm$^{-1}$.

(iii) Preparation of p-Nitrobenzyl 3-methyl-7-oxo-1-azabicyclo[3,2,0]hept-2-ene-2-carboxylate

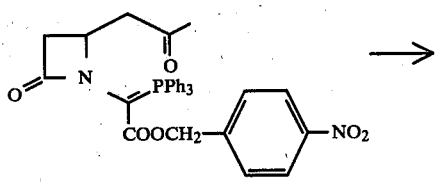 →

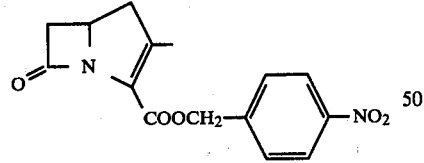

(73)

The phosphorane (72) (0.2 g, 0.345 mmoles) was heated in dry toluene (10 ml) under argon for 10 hours at 100° C. The toluene was removed under reduced pressure and the residue chromatographed (silica eluted with pet. ether-ethyl acetate) to give the bicyclic product (73) (0.05 g, 64%) as colourless needles m.p. 116° (from ethyl acetate pet. ether) having $\nu_{max}$ (CHCl$_3$) 3000, 1785, 1725, 1635, 1610, 1415, and 1350 cm$^{-1}$, δ(CDCl$_3$) 2.12 (3H, s, CH$_3$), 2.7–3.0 (3H, m, C4-H and C-6H), 3.4 (1H, dd, J 6, 16 Hz, C6-H), 4.12 (1H, m, C5-H), 5.3 (2H, ABq, J 14 Hz, benzylic) and 7.45–8.25 (4H, m, aromatic) and unchanged phosphorane (0.05 g).

EXAMPLE 24

Methyl 7-oxo-1-azabicyclo[3,2,0]hept-2-ene-2-carboxylate

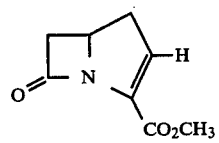

(i) Preparation of 4-allyl-1-(1-hydroxy-1-methoxycarbonylmethyl(azetidin-2-one

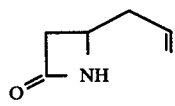 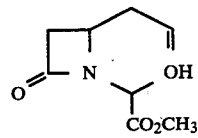

(18)        (74)

Methyl glyoxylate hydrate (9.75 g) in benzene (500 ml) was refluxed for 1 hour in a Dean-Stark apparatus to remove the water. The azetidinone (18) (2.68 g) was then added and the reaction mixture refluxed for 2 hours. A further portion of the azetidinone (1.34 g) (18) was then introduced, and refluxing continued for 3 hours. Chromatography of the crude product as in Example 4 (iv) gave the alcohol (74) as a pale yellow oil (5.33 g). $\nu_{max}$ (CHCl$_3$) 3500, 3350 (broad), 1760–1740 (strong), 1640 (weak) cm$^{-1}$. δppm (CDCl$_3$) 2.24–2.90 (3H, m, including [1H, dd, J3 Hz. 14.5 Hz at δ2.68]), 3.11 (1H, dd, J4.5 Hz, 14.5 Hz), 3.72–4.42 (5H, including [3H, s, at δ3.90], 1H, exch. D$_2$O), 5.00–6.29 (4H, m including [1H, s, at δ5.48]).

(ii) Preparation of 4-allyl-1-(1-methoxycarbonyl-1-triphenylphosphoranylidenemethyl)azetidin-2-one

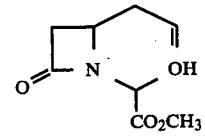 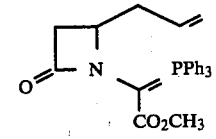

(74)        (75)

A stirred solution of the alcohol (74) (5.23 g) in dry tetrahydrofuran (150 ml) under argen, was cooled to −20°, and treated with lutidine (6.06 ml) in tetrahydrofuran (20 ml). Thionyl chloride (3.83 ml) in tetrahydrofuran (20 ml) was added dropwise. After allowing to reach 0° over 20 minutes, the solution was filtered, the lutidine hydrochloride being washed with toluene.

The combined filtrate and washings were evaporated to dryness. The residue was taken up in dry dioxan (150 ml) and treated with lutidine (6.06 ml) and triphenylphosphine (13.7 g). After stirring at room temperature, overnight, the phosphorane (75) was isolated as in Example 4 (v) and obtained as white crystals (7.3 g) from ether m.p. 208°–212°. $\nu_{max}$ (CHCl$_3$) 1738, 1640, 1620 cm$^{-1}$ (Found: C, 72.6; H, 5.9; N, 3.0%. C$_{27}$H$_{26}$NO$_3$P requires C, 73.1; H, 5.9; N, 3.2%).

(iii) Preparation of methyl 7-oxo-1-azabicyclo[3,2,0]hept-2-ene-2-carboxylate

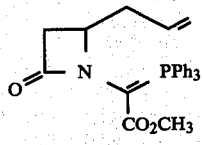 

(75)  (76)

The phosphorane (75) (0.886 g) in ethyl acetate (60 ml) was treated with trifluoroacetic acid (1.52 ml). After cooling to −70°, ozone was passed into the solution until it became pale blue. After passing argon through to remove excess ozone, triphenylphosphine (534 mg) in ethyl acetate (5 ml) was added. After stirring for 10 minutes the reaction flask was transferred to an ice-bath and saturated aqueous sodium bicarbonate (50 ml) was added. The mixture was stirred vigorously for 1 hour, and then extracted and chromatographed as in Example (21,iii) to give the bicyclic compound (76) (150 mg). Crystallisation from ethyl acetate/petroleum ether (60°–80°) gave (76) as pale yellow needles, m.p. 72°–72.5°. ν$_{max}$ (CHCl$_3$) 1785, 1738. λ$_{max}$ (EtOH) 272 nm (ε4,500). δppm (CDCl$_3$) 2.66 (1H, ddd, J 3 Hz, 8.5 Hz, 19 Hz), 3.04 (1H, ddd, J 3 Hz, 11.5 Hz, 19 Hz), 2.90 (1H, dd, J 3 Hz, 16.5 Hz), 3.45 (1H, dd, J 5.5 Hz, 16.5 Hz), 3.79 (3H, s), 4.23 (1H, m), 6.43 (1H, t, J 3 Hz) (Found: C, 57.47; H, 5.63; N, 8.24% C$_8$H$_9$NO$_3$ requires C, 57.49; H, 5.39; N, 8.38%) (Found: M, 167.0589 C$_8$H$_9$NO$_3$ requires M, 167.0582).

EXAMPLE 25 p-Nitrobenzyl 7-oxo-1-azabicyclo[3,2,0]hept-2-ene-2-carboxylate

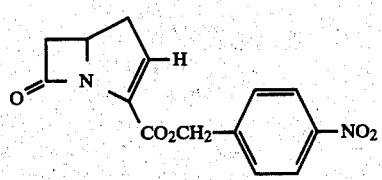

(i) Preparation of 4-allyl-1-(1-hydroxy-1-p-nitrobenzyloxycarbonylmethyl)azetidin-2-one

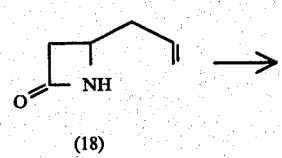

(18)

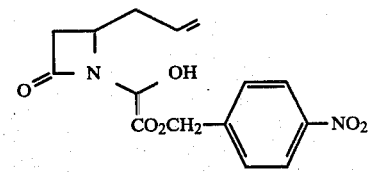

(77)

p-Nitrobenzyl glyoxylate hydrate (6.8 g) in benzene (120 ml) was refluxed for one hour with removal of water (Dean-Stark). The azetidinone (18) (3 g) was added and the mixture refluxed for two hours. The solution was cooled, the solvent evaporated and the residue chromatographed. Elution with 80% ethyl acetate/petroleum ether 860°–80°) gave the product (77). The product was re-chromatographed to complete purification and collected as an oil (3.2 g) (37%) ν$_{max}$ (CHCl$_3$) 3500 (OH), 1755 (br), 1530, 1355 cm$^{-1}$. δppm (CDCl$_3$) 2.39 (2H, m, CH$_2$CH═CH$_2$), 2.61 (1H, dd, J 16 Hz, 4 Hz, C3-H), 3.05 (1H, dd, J 16 Hz, 6 Hz, C3-H), 3.92 (1H, m, C4-H), 4.63 (1H, m, collapsing to a singlet on D$_2$O exchange, CH-OH), 4.80 to 5.80 (6H, complex pattern including CH$_2$Ph-p-NO$_2$ at 5.35, OH [exchangeable] and CH═CH$_2$), 7.56 and 8.23 (4H, ABq, J 8 Hz, aromatics.)

(ii) Preparation of 4-allyl-1-(1-p-nitrobenzyloxycarbonyl-1-triphenylphosphoranylidenemethyl)azetidine-2-one

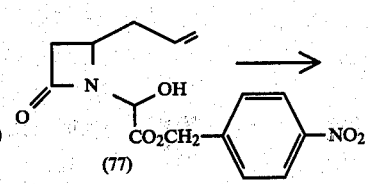

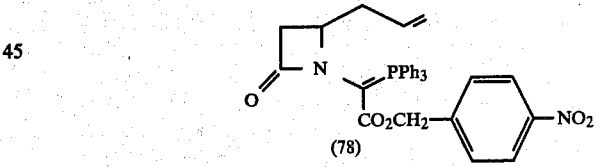

(78)

A stirred solution of the alcohol (77) (1.6 g) in dry THF (100 ml) was treated with 2,6 lutidine (1.07 g) and thionyl chloride (1.19 g) in THF (20 ml) at −20° and stirring continued for 20 minutes. The mixture was filtered, the solvent evaporated and the residue azeotroped twice with toluene. It was dissolved in dioxan (100 ml) and 2,6-lutidine (1.01 g) and triphenylphosphine (2.62 g) were added. The reaction was stirred at room temperature overnight and filtered. The solvent was evaporated and the residue chromatographed to yield the product, (78) after de-colourising with charcoal (ethanol/ethyl acetate solution) and trituration of the evaporated solution with ether, as a light yellow solid (1.5 g; 53%) m.p. 182°–3° ν$_{max}$ (CHCl$_3$) 1740, 1620, 1525, 1355 cm$^{-1}$. (Found: C, 70.26; H, 5.33; N, 4.80. C$_{33}$H$_{29}$N$_2$O$_5$P requires C, 70.21; H, 5.14; N, 4.96%).

(iii) Preparation of p-nitrobenzyl 7-oxo-1-azabicyclo[3,2,0]hept-2-ene-2-carboxylate

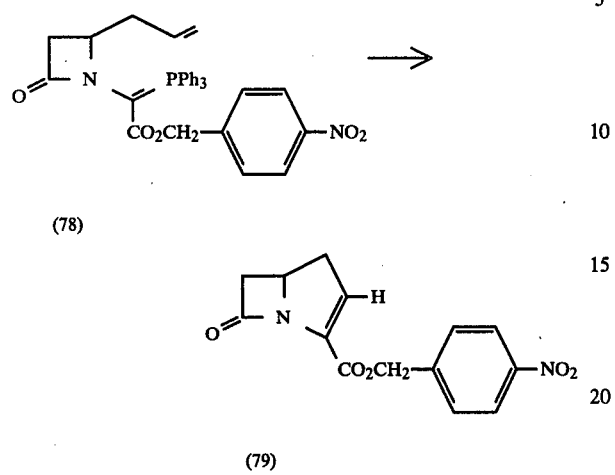

(78)

(79)

The phosphorane (78) (1.0 g) in ethyl acetate (50 ml) was treated with trifluoroacetic acid (1.5 ml) (R.T.) and then cooled to −70°. Ozone was passed through the solution until it became slightly blue. Excess ozone was then removed by bubbling through argon, and then triphenylphosphine (0.51 g) in ethyl acetate (10 ml) was added. The reaction flask was transferred to an ice-bath and the reaction solution stirred vigorously and treated with aqueous sodium bicarbonate solution until slightly basic (pH 8). The organic phase was separated, dried (MgSO₄), filtered and left to stand at room temperature for 2.5 h. The solution was evaporated to a gum and chromatographed on silica gel (Merck 60<230 mesh) eluting with 1:1 ethyl acetate-petroleum ether (60°–80°). The product (79) was obtained as a yellow crystalline solid (0.21 g; 41%), m.p. 144°–147°; $\lambda_{max}$ (EtOH) 270 nm ($\epsilon$, 13,550), $\nu_{max}$ (CDCl₃) 1780, 1730, 1610, 1525, 1350 cm$^{-1}$. $\delta$ppm (CDCl₃) 2.55–3.15 (2H, m, C4-H₂), 2.95 (1H, dd, J 16 Hz, 3 Hz, C6-H), 3.50 (1H, dd, J 16 Hz, C6-H), 4.10–4.40 (1H, m, C5-H), 5.21 and 5.41 (2H, ABq, J 12 Hz, CH₂PhpNO₂), 6.53 (1H, t, J 2.5 Hz), 7.55 (2H, d, J 8 Hz), 8.15 (2H, d, J 8 Hz) (Found: C, 58.2; H, 4.2; N, 9.5%; M, 288.0773 C₁₄H₁₂N₂O₅ requires C, 58.3; H, 4.2; N, 9.7%; M, 288.0746).

EXAMPLE 26

Phthalidyl 7-oxo-1-azabicyclo[3,2,0]hept-2-ene-2-carboxylate

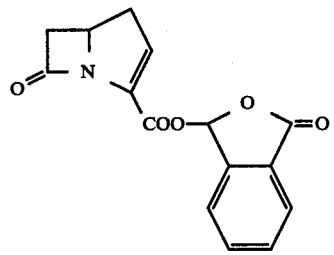

(i) Preparation of 4-allyl-1-(1-phthalidyloxycarbonyl-1-tris-p-methoxyphenylphosphoranylidenemethyl)azetidin-2-one

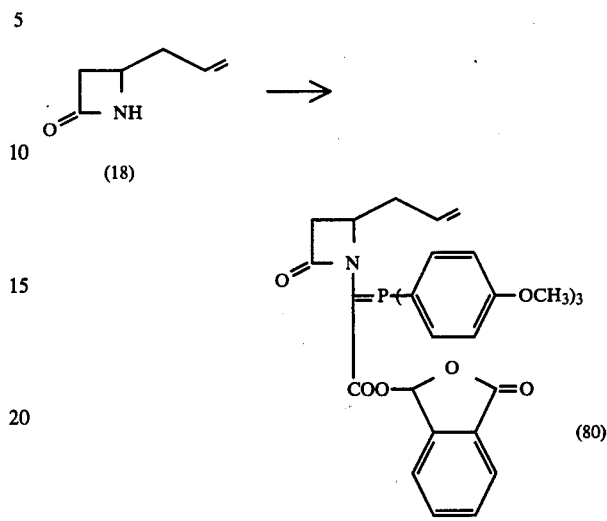

(18)

(80)

Allylazetidinone (18) (6.3 g), glyoxylic acid monohydrate (5.52 g), 30 4A° molecular sieves (⅛″ pellets) and dry DMF (30 ml) were stirred for 6 hours at room temperature. The mixture was cooled to 0° C. and powdered potassium carbonate (4.14 g) was added. The mixture was allowed to warm up to room temperature and stirred for 5 minutes. Bromophthalide (12.8 g) was added and the mixture was stirred for 16 hours. The resulting solution was poured onto N/10 hydrochloric acid (250 ml) and ethyl acetate (250 ml). The organic layer was washed once more with N/10 hydrochloric acid (250 ml) and then with saturated aqueous sodium hydrogen carbonate (250 ml) and brine (250 ml); each aqueous washing being extracted once with ethyl acetate (250 ml). The combined organic extracts were dried (Na₂SO₄) and the solvent removed under reduced pressure to give an oil (10 g).

A stirred solution of this oil in dry tetrahydrofuran (250 ml), under argon, was cooled to −20°, and treated with 2,6-lutidine (7.6 ml) followed by thionyl chloride (4.8 ml in 30 ml tetrahydrofuran). After stirring for 20 minutes at −20° the mixture was brought to room temperature and filtered. The precipitated solid was washed with toluene and the combined filtrate and washings were evaporated to dryness under reduced pressure. The residue was dissolved in toluene and re-evaporated to dryness to remove excess thionyl chloride.

The oil obtained was dissolved in dry tetrahydrofuran (250 ml) and treated with 2,6-lutidine (7.6 ml) and tris-p-methoxyphenylphosphine (15 g). After stirring for 16 hours, the mixture was filtered and the solvent removed from the filtrate under reduced pressure. The filtrant was dissolved up in ethyl acetate (250 ml) and N/10 hydrochloric acid (250 ml) and added to the evaporated filtrate. The organic layer was separated and washed with N/10 hydrochloric acid (250 ml) and brine; each aqueous washing being extracted with ethyl acetate (250 ml). The combined organic extracts were dried (Na₂SO₄) and the solvent removed under reduced pressure. Chromatography on silica gel eluting with petroleum ether - ethyl acetate - dioxan mixtures gave the required phosphorone (80), initially as a foam (10 g), which crystallised on addition of ether; (6.25 g); m.p. 136–9° (ethyl acetate - petroleum ether); $\nu_{max}$ (CHCl$_3$) 3000, 1780, 1745, 1650, 1605, 1260, and 1115 cm$^{-1}$; (Found: C, 64.98; H, 5.24; N, 2.13. C$_{37}$H$_{34}$PNO$_8$. 2H$_2$O requires C, 64.68; H, 5.58; N, 2.04%).

(ii) Preparation of phthalidyl 7-oxo-1-azabicyclo[3,2,0]-hept-2-ene-2-carboxylate

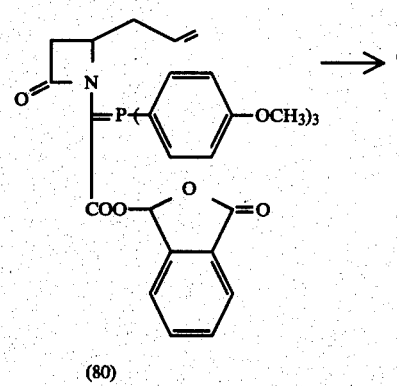

(80)

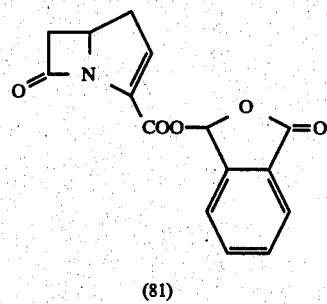

(81)

The phosphorane (80) (0.325 g) was dissolved in 5:1 ethyl acetate/trifluoroacetic acid (12 ml). The solution was left at room temperature for 10 minutes and then cooled to −70°. Ozone was then passed through the solution until it became pale blue. Argon was passed through the solution to remove excess ozone and then tris-p-methoxyphenylphosphine (0.17 g) in ethyl acetate (2 ml) was added. The mixture was warmed up to 0° C. with an ice bath and then saturated potassium hydrogen carbonate solution (10 ml) was added carefully with vigorous agitation. The layers were separated and the aqueous layer was extracted twice more with ethyl acetate (2×10 ml). The combined organic layers were pre-dried (Na$_2$SO$_4$) and then left standing over 4A° molecular sieves and di- isopropylaminomethylpolystyrene (0.4 g) for 16 hours. The solution was filtered and the solvent removed under reduced pressure to give a yellow oil. Rapid chromatography on florisil eluting with 1:1 petroleum ether - ethyl acetate give the phthalidyl ester (81) as a white solid (17 mgms) having $\nu_{max}$ (CHCl$_3$) 1800, 1755, 1615 m and 985 cm$^{-1}$, δ(CDCl$_3$) 2.7–3.2 (3H, m, C4-H$_2$ and C6-H$_A$), 3.50 (1H, 2×dd, J 6, 17 Hz, C6-H$_B$), 4.23 (1H, m, C5-H), 6.49 and 6.62 (1H, 2×t, J 3 Hz, C3-H), 7.45 and 7.51 (1H, 2×s, phthalidyl methine), and 7.55–7.95 (4H, m, aromatic).

The concentrations of this compound required to inhibit the growth of the following bacteria are given below:

| Organism | µg/ml (agar) |
|---|---|
| B. subtilis A | 20 |
| Citrobacter freundii E8 | 20 |
| Enterobacter cloacae N1 | 20 |
| E. coli 0111 | 20 |
| Klebsiella aerogenes A | 20 |
| Proteus mirabilis C977 | 20 |
| Pseudomonas aeruginosa A | 160 |
| Salmonella typhimurium CT10 | 20 |
| Serratia marcescens VS20 | 20 |
| Staph. aureus Oxford | 20 |
| Staph. aureus Russell | 20 |

EXAMPLE 27

Pivaloyloxymethyl 7-oxo-1-azabicyclo[3,2,0]hept-2-ene-2-carboxylate

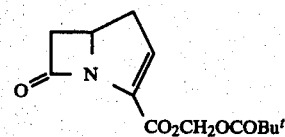

(i) 4-Allyl-1-(1-pivaloyloxymethoxycarbonyl-1-triphenylphosphoranylidenemethyl)azetidine-2-one

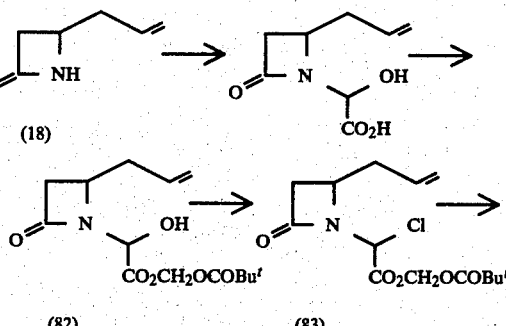

(18)    (82)    (83)

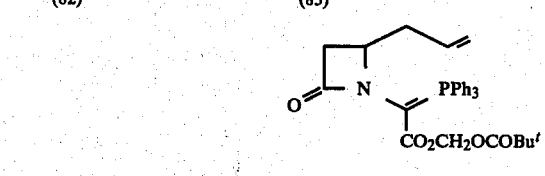

(84)

4-Allylazetidin-2-one (18) (2.0 g) and glyoxylic acid monohydrate (1.75 g) were stirred together in dry dimethylformamide (10 ml) for 6 hours in the presence of 4A molecular sieves. The mixture was then cooled in an ice bath and powdered potassium carbonate (1.31 g) was added. It was allowed to warm to room temperature and stirred for 5 minutes prior to adding pivaloyloxymethyl bromide (5.3 g). The reaction was stirred overnight and then poured into a mixture of N/10 hydrochloric acid (80 ml) and ethyl acetate (80 ml). The organic phase was separated and the aqueous solution washed with further ethyl acetate (50 ml). The ethyl acetate solutions were combined, washed with saturated aqueous sodium bicarbonate, then brine and dried over sodium sulphate. It was concentrated in vacuo to give the crude ester (82) as a yellow oil (4.7 g).

The crude ester (82) (4.7 g) was dissolved in dry tetrahydrofuran (80 ml) and stirred at −20° under argon. It was treated with 2,6-lutidine (3.7 ml) followed over a period of 5 minutes by a solution of thionyl chloride (2.3 ml) in tetrahydrofuran (20 ml). The reaction was allowed to warm to ambient temperature over a period of ½ hour and then filtered. The solid was washed with dry toluene and the combined filtrates was concentrated under reduced pressure. The vestigial thionyl chloride was removed by two further evaporations from toluene to give the chloride (83) as a brown oil.

The chloride (83) was dissolved in dry dioxane (80 ml) and treated with triphenylphosphine (8.2 g) and 2,6-lutidine (3.7 ml). The reaction mixture was stirred overnight and then filtered; the filtrate concentrated and redissolved in ethyl acetate (100 ml). This solution was washed free of base with N/10 hydrochloric acid (ca 100 ml) and then washed with brine and dried over sodium sulphate. The solution was concentrated and then chromatographed on silica gel 60 (<230 mesh) eluting with ethyl acetate/60°-80° petroleum ether 7:3 to give a foam. This was dissolved in diethyl ether (20 ml) and a white solid rapidly crystallized out. This was 4-allyl-1-(1-pivaloyloxymethoxycarbonyl-1-triphenylphosphoranylidenemethyl)azetidine-2-one (84) which was obtained in a yield of 3.06 g; m.p. 140°-142° (ethyl acetate/60°-80° petroleum ether); $\nu_{max}$ (CHCl$_3$) 2980, 1740 and 1635 cm$^{-1}$.

(ii) Pivaloyloxymethyl 7oxo-1-azabicyclo[3,2,0]hept-2-ene-2-carboxylate

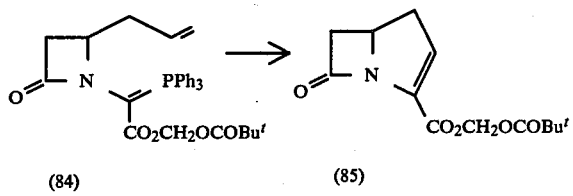

A solution of 4-allyl-1-(1-pivaloyloxymethoxycarbonyl-1-triphenylphosphoranylidenemethyl)azetidine-2-one (84) (0.50 g) in ethyl acetate (15 ml) was stirred in a bath at 10° and treated with trifluoroacetic acid (3 ml). After 15 minutes the solution was cooled to −78° and ozone was passed through the solution until reaction was complete. Excess ozone was blown off in a stream of argon and an ethyl acetate solution of triphenylphosphine (0.24 g) was added. After a period of 30 minutes the reaction flask was transferred to an ice bath and ethyl acetate (40 ml) followed by saturated aqueous sodium bicarbonate (90 ml) were added with vigorous stirring. The ethyl acetate phase was then immediately separated, washed with brine and dried by stirring over calcium chloride for 15 minutes. The solution was then filtered and 4A molecular sieves added to the solution. The supernatent solution was concentrated 3 hours later and quickly chromatographed on a small column of silica gel 60 (<230 mesh) eluting with ethyl acetate/60°-80° petroleum ether 1:1. Further purification was effected on a small column of Florisil (200-300 mesh) eluting with ethyl acetate/60°-80° petroleum ether 3:7. This gave pivaloyloxymethyl 7-oxo-1-azabicyclo[3,2,0-]hept-2-ene-2-carboxylate (85) (0.022 g) as a colourless gum; $\nu_{max}$ (CHCl$_3$) 2970, 1790, 1750 and 1610 cm$^{-1}$; $\tau$(CDCl$_3$) 3.51 (1H, t, J 3 Hz, C3-H), 4.15 and 4.24 (2H, ABq, J 5½ Hz, OCH$_2$O), 5.78 (1H, tdd, J 9, 5½ and 3 Hz, C5-H), 6.54 (1H, dd, J 17 and 5½ Hz, C6-H), 7.03 (1H, ddd, J 19, 9 and 3 Hz, C4-H), 7.10 (1H, dd, J 17 and 3 Hz, C6-H), 7.31 (1H, ddd, J 19, 9 and 3 Hz, C4-H) and 8.80 (9H, s, t-butyl). (M+ at m/e 267.1118. C$_{13}$H$_{17}$NO$_5$ requires 267.1107).

What we claim is:
1. A compound of the formula (II):

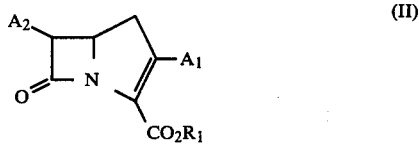

wherein R$_1$ is alkyl of up to 12 carbon atoms, alkenyl of up to 8 carbon atoms, phenyl, benzyl or said alkyl, alkenyl, phenyl or benzyl mono-substituted by lower alkoxyl, lower alkanoyloxyl, halo or nitro; or R$_1$ is a group of the sub-formula (a) or (b):

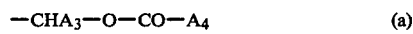

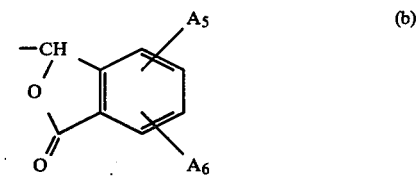

wherein A$_3$ is hydrogen or methyl; A$_4$ is lower alkyl, lower alkoxyl, phenyl, phenoxyl, benzyl or benzyloxyl; A$_5$ is hydrogen, methyl or methoxyl; and A$_6$ is hydrogen, methyl or methoxyl; A$_1$ is hydrogen; and A$_2$ is a group CR$_2$R$_3$R$_4$ wherein R$_2$ is hydrogen or hydroxyl; and R$_4$ is joined to R$_3$ to form part of a 5- to 7- carbon atom carbocyclic ring.

2. A compound according to claim 1 which has the cis-configuration about the β-lactam ring.

3. A compound according to claim 1 which has the transconfiguration about the β-lactam ring.

4. A compound according to claim 1 wherein R$_1$ is alkyl of up to 12 carbon atoms, alkenyl of up to 8 carbon atoms, phenyl, benzyl or said alkyl, alkenyl, phenyl or benzyl mono-substituted by lower alkoxyl, lower alkanoyloxyl, halo or nitro.

5. A compound according to claim 1 wherein R$_1$ is lower alkyl unsubstituted or mono-substituted by lower alkoxyl.

6. A compound according to claim 1 wherein R$_1$ is benzyl unsubstituted or mono-substituted by lower alkoxyl, nitro or chloro.

7. A compound according to claim 1 wherein R$_1$ is a group of the sub-formula (a) or (b):

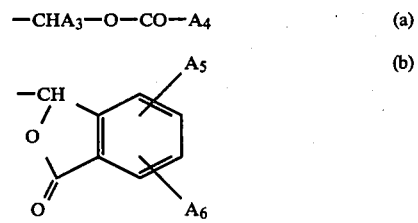

wherein A$_3$ is hydrogen or methyl; A$_4$ is lower alkyl, lower alkoxyl, phenyl, phenoxyl, benzyl or benzyloxyl;

A5 is hydrogen, methyl or methoxyl; and A6 is hydrogen methyl or methoxyl.

8. A compound according to claim 1 wherein $R_1$ is benzyl.

9. A compound according to claim 1 wherein $R_1$ is p-nitrobenzyl.

10. A compound according to claim 1 wherein $R_1$ is phthalidyl.

11. A pharmaceutical composition useful for treating bacterial infections in humans and animals which comprises an antibacterially effective amount of a compound of the formula (II):

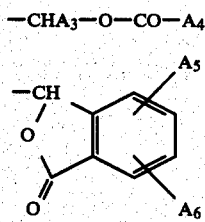
(II)

wherein $R_1$ is alkyl of up to 12 carbon atoms, alkenyl of up to 8 carbon atoms, phenyl, benzyl or said alkyl, alkenyl, phenyl or benzyl mono-substituted by lower alkoxyl, lower alkanoyloxyl, halo or nitro; or $R_1$ is a group of the sub-formula (a) or (b):

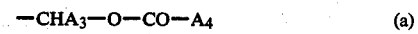 (a)

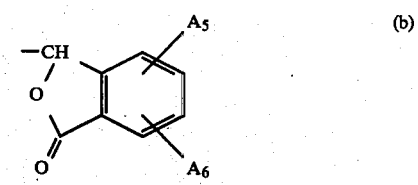 (b)

wherein $A_3$ is hydrogen or methyl; $A_4$ is lower alkyl, lower alkoxyl, phenyl, phenoxyl, benzyl or benzyloxyl; $A_5$ is hydrogen, methyl or methoxyl; and $A_6$ is hydrogen, methyl or methoxyl; $A_1$ is hydrogen; and $A_2$ is a group $CR_2R_3R_4$ wherein $R_2$ is hydrogen or hydroxyl; and $R_4$ is joined to $R_3$ to form part of a 5- to 7-carbon atom carbocyclic ring, in combination with a pharmaceutically acceptable carrier.

12. A composition according to claim 11 wherein $R_1$ is alkyl of up to 12 carbon atoms, alkenyl groups of up to 8 carbon atoms, phenyl, benzyl or said alkyl, alkenyl, phenyl or benzyl mono-substituted by lower alkoxyl, lower alkanoyloxyl, halo or nitro.

13. A composition according to claim 11 wherein $R_1$ is lower alkyl unsubstituted or mono-substituted by lower alkoxyl.

14. A composition according to claim 11 wherein $R_1$ is benzyl unsubstituted or mono-substituted by lower alkoxyl, nitro or chloro.

15. A composition according to claim 11 wherein $R_1$ is a group of the sub-formula (a) or (b):

$-CHA_3-O-CO-A_4$ (a)

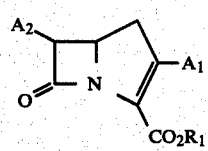 (b)

wherein $A_3$ is hydrogen or methyl, $A_4$ is lower alkyl, lower alkoxyl, phenyl, phenoxyl, benzyl or benzyloxyl; $A_5$ is hydrogen, methyl or methoxyl; and $A_6$ is hydrogen, methyl or methoxyl.

16. A composition according to claim 11 wherein $R_1$ is benzyl.

17. A composition according to claim 11 wherein $R_1$ is p-nitrobenzyl.

18. A composition according to claim 11 wherein $R_1$ is phthalidyl.

19. A composition according to claim 11 in parenteral administration form.

20. A composition according to claim 11 for the treatment of mastitis in cattle in intra-mammary administration form.

* * * * *